(12) United States Patent
Suzuki et al.

(10) Patent No.: US 8,147,475 B2
(45) Date of Patent: *Apr. 3, 2012

(54) DISPOSABLE WEARING ARTICLE

(75) Inventors: Sachiyo Suzuki, Kagawa-ken (JP);
Yoshitaka Mishima, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 977 days.

This patent is subject to a terminal disclaimer.

(21) Appl. No.: 11/315,278

(22) Filed: Dec. 23, 2005

(65) Prior Publication Data

US 2006/0142727 A1    Jun. 29, 2006

(30) Foreign Application Priority Data

Dec. 27, 2004  (JP) ................................ 2004-376412

(51) Int. Cl.
*A61F 13/15* (2006.01)
*A61F 13/20* (2006.01)

(52) U.S. Cl. ......... 604/385.24; 604/385.01; 604/385.19; 604/385.27

(58) Field of Classification Search ............ 604/385.08, 604/385.101, 385.24–385.3, 385.19, 348
See application file for complete search history.

(56) References Cited

U.S. PATENT DOCUMENTS

| | | | | |
|---|---|---|---|---|
| 4,695,278 A | * | 9/1987 | Lawson | 604/385.27 |
| 4,704,116 A | * | 11/1987 | Enloe | 604/385.27 |
| 4,738,677 A | * | 4/1988 | Foreman | 604/385.27 |
| 5,275,590 A | * | 1/1994 | Huffman et al. | 604/385.27 |
| 5,593,401 A | * | 1/1997 | Sosalla et al. | 604/385.28 |
| 5,653,703 A | * | 8/1997 | Roe et al. | 604/385.01 |
| 5,814,036 A | * | 9/1998 | Ronnberg et al. | 604/385.201 |
| 6,103,952 A | * | 8/2000 | Coles et al. | 604/358 |
| 6,156,022 A | * | 12/2000 | Hedlund | 604/385.29 |
| 6,222,092 B1 | * | 4/2001 | Hansen et al. | 604/378 |
| 6,406,465 B1 | * | 6/2002 | Otsubo | 604/385.01 |
| 6,423,048 B1 | * | 7/2002 | Suzuki et al. | 604/385.28 |
| 6,790,203 B2 | * | 9/2004 | Een | 604/385.28 |
| 6,824,534 B2 | * | 11/2004 | Mishima et al. | 604/385.01 |
| 2002/0013567 A1 | * | 1/2002 | Mishima et al. | 604/385.101 |
| 2004/0181202 A1 | | 9/2004 | Corneliusson | |

(Continued)

FOREIGN PATENT DOCUMENTS

DE            19534826 A1  *  3/1997

(Continued)

OTHER PUBLICATIONS

European Search Report for European Application No. 05816899.8 mailed Nov. 23, 2009.

*Primary Examiner* — Tatyana Zalukaeva
*Assistant Examiner* — Susan Su
(74) *Attorney, Agent, or Firm* — Lowe, Hauptman, Ham & Berner, LLP

(57) ABSTRACT

A disposable wearing article is provided with a pair of liquid-barrier sheets on a body-side surface of the article. A dimension by which distal edges of distal zones of the barrier sheets are spaced from each other in a transverse direction is gradually enlarged from a rear end toward a front end of the article. An end sheet functioning to pull the distal zones closer to each other in the transverse direction is attached to the distal zones extending toward the rear end so as to extend between the distal zones.

11 Claims, 18 Drawing Sheets

U.S. PATENT DOCUMENTS

| | | |
|---|---|---|
| 2005/0055004 A1 | 3/2005 | Turi et al. |
| 2006/0135931 A1* | 6/2006 | Suzuki et al. ............ 604/385.19 |
| 2006/0142727 A1* | 6/2006 | Suzuki et al. ............ 604/385.19 |

FOREIGN PATENT DOCUMENTS

| | | | |
|---|---|---|---|
| EP | 0374542 A2 | | 11/1989 |
| EP | 0 955 028 | | 11/1999 |
| EP | 1 025 825 A2 | | 8/2000 |
| EP | 1025825 A2 | * | 8/2000 |
| JP | 02-65861 | | 3/1990 |
| JP | 03-136654 A | | 6/1991 |
| JP | 3136654 A | * | 6/1991 |
| JP | 07-184955 | | 7/1995 |
| JP | 08-010287 | | 1/1996 |
| JP | 8 322 878 | | 12/1996 |
| JP | 10-314222 | | 12/1998 |
| TW | 330840 | * | 5/1998 |
| WO | WO 9214429 A1 | * | 9/1992 |
| WO | 94/28844 | | 12/1994 |
| WO | 95/25493 | | 9/1995 |
| WO | WO 9942066 A1 | * | 8/1999 |

\* cited by examiner

DISPOSABLE WEARING ARTICLE

RELATED APPLICATIONS

The present application is based on, and claims priority from, Japanese Application Number 2004-376412, filed Dec. 27, 2004, the disclosure of which is hereby incorporated by reference herein in its entirety.

BACKGROUND OF THE INVENTION

The present invention relates to a disposable wearing article adapted for absorption and containment of urine as well as feces.

In Japanese Unexamined Patent Application Publication No. 1996-322878 (hereinafter referred to as "JP'878"), there has already been proposed a disposable diaper comprising a liquid-pervious topsheet, a liquid-impervious backsheet and a liquid-absorbent core sandwiched between these sheets so as to define, in a longitudinal direction, a front waist region, a rear waist region and a crotch region extending between these waist regions. The diaper includes a pair of liquid-barrier sheets spaced from each other by a predetermined dimension in a transverse direction and extending in the longitudinal direction and a pair of liquid partition sheets spaced from each other by a predetermined dimension in the longitudinal direction and extending in the transverse direction.

The barrier sheets respectively comprise proximal zones bonded to the opposite lateral margins of the diaper and extending in the longitudinal direction, distal zones extending in the longitudinal direction in parallel to the proximal edges and normally biased to rise up above the topsheet, and front and rear ends bonded to the front and rear waist regions with inner surfaces of these ends opposed to these regions. Distal edges of the respective distal zones are provided with stretchable and contractible elastic members extending in the longitudinal direction. The distal zones of the respective barrier sheets form barriers functioning to prevent urine and/or feces from moving sideways and thereby to prevent urine and/or feces from leaking beyond the opposite side edges of the diaper. The partition sheets are located substantially in the longitudinal middle of the crotch region, each comprising a lower segment bonded to the topsheet and an upper segment having transversely opposite ends bonded to the distal zones of the barrier sheets. Upper edges of the respective upper segments are provided with stretchable and contractible elastic members extending in the transverse direction in a stretchable and contractible manner. The upper segments of the respective partition sheets rise up above the topsheet as the distal zones of the respective barrier sheets rise up to form barriers functioning to intercept movement of urine from the front waist region toward the rear waist region and simultaneously to intercept movement of feces from the rear waist region toward the front waist region.

In the JP'878, while it may be possible for the distal zones of the respective barrier sheets to prevent feces from moving sideways, these distal zones are not adapted to cover feces received by the diaper from above. This means that feces discharged in the diaper may be exposed between these barrier sheets and readily come in contact with the wearer's crotch region and buttock. Consequentially, feces may cling to the wearer's crotch region and buttock and the wearer's skin may be soiled with such feces over a wide area.

SUMMARY OF THE INVENTION

In view of the problem as has been described above, it is an object of the present invention to provide a disposable wearing article improved so that a wearer can use the article without anxiety that feces discharged in the article might cling to the wearer's inguinal region as well as buttock and the wearer's skin might be soiled with feces.

The object set forth above is achieved, according to the present invention, by a disposable wearing article comprising a front waist region, a rear waist region, a crotch region extending between these waist regions, a pair of longitudinally opposite ends extending in a transverse direction, a pair of transversely opposite lateral margins extending in a longitudinal direction, and a pair of liquid-barrier sheets laid on a body-side surface of at least the crotch region among the front and rear waist regions and the crotch region. The barrier sheets comprise proximal zones lying along the lateral margins of the article so as to extend in the longitudinal direction, elasticized distal zones extending in the longitudinal direction and normally biased to rise up above the body-side surface, and longitudinally opposite front and rear ends bonded to the body-side surface.

The present invention further comprises a dimension by which distal edges of the distal zones are spaced from each other being gradually enlarged from the rear ends toward the front ends of the barrier sheets.

With this article put on the wearer's body, the edges of the distal zones of the barrier sheets come closer to or in contact with the wearer's inguinal region and further extend into the wearer's buttock cleavage so as to come closer to or in contact with both sides of the anus. A feces receiving space is formed between the body-side surface and the distal edges of the distal zones of the respective barrier sheets extending aside toward the rear ends. Feces discharged in the article are received in this feces receiving space through the clearance defined between these edges. Thereupon the distal edges of the distal zones extending aside toward the rear ends of the respective barrier sheets cover feces from above. Urine discharged between the distal zones of the respective barrier sheets is absorbed through the body-side surface and contained therein.

The present invention may include preferred embodiments as follows: A liquid-absorbent core adapted for absorption and containment of bodily fluids is sandwiched between the body-side surface and the garment-side surface at least in the crotch region of the front and rear waist regions and the crotch region, a minimum dimension by which distal edge of the distal zones are spaced from each other being in a range of 0 to 25% of the minimum transverse dimension of the core extending in the crotch region and the maximum dimension by which distal edge of the distal zones are spaced from each other being in a range of 26 to 120% of the minimum transverse dimension of the core extending in the crotch region.

The article further comprises an elasticized end sheet laid aside toward the rear ends between the distal zones and functioning to pull the distal zones closer to each other wherein the end sheet comprises opposite lateral segments bonded to the distal zones and an intermediate segment extending between the opposite lateral segments.

The elasticized end sheet further comprises an edge extending between the rear ends and bonded to the rear ends as well as to the body-side surface so that a pocket opening from the rear ends toward a longitudinal middle of the crotch region is formed between the body-side surface and the end sheet.

The barrier sheets have the front and rear ends bonded to the body-side surface with the front ends folded outward in the transverse direction and with inner edges of the rear ends directed inward in the transverse direction.

In the disposable wearing article according to the present invention, the feces receiving space is formed between the body-side surface and the distal zones of the barrier sheets extending aside toward the side of the rear ends so that feces discharged in the article is received in this feces receiving space through the clearance defined between the edges of the respective distal zones and the distal zones of the respective barrier sheets extending aside toward the side of the rear ends cover feces from above. Consequentially, it is unlikely that feces might be significantly exposed between the barrier sheets and cling to the wearer's crotch region and buttock. In this way, the wearer's skin is protected from soil with feces. In this article, the dimension by which the edges of the distal zones are spaced from each other is gradually enlarged from the side of the rear ends toward the side of the front ends. Such an arrangement prevents urination from occurring outside the distal zones. In addition, urine discharged in the article is prevented by the distal zones of the barrier sheets from moving sideways and leaking beyond the opposite lateral margins of the article.

With the article in which the minimum dimension by which distal edges of the distal zones are spaced from each other is in a range of 0 to 25% of the minimum transverse dimension of the core extending in the crotch region and the maximum dimension by which distal edges of the distal zones are spaced from each other is in a range of 26 to 120% of the minimum transverse dimension of the core extending in the crotch region, it is ensured that the distal zones of the barrier sheets extending aside toward the side of the rear ends cover feces discharged in the article from above and thereby prevent feces from being exposed between the barrier sheets. Consequentially, there is no anxiety that feces might cling to the wearer's inguinal region and buttock and the wearer's skin might be soiled with feces. This article allows the distal zones of the respective barrier sheets extending aside toward the side of the front ends to prevent urine discharged in the article from moving sideways and leaking beyond the opposite lateral margins of the article.

With the article including the elasticized end sheet laid between the distal zones extending aside toward the side of the rear ends, even if the distal zones extending aside toward the side of the rear ends tend to move in the transverse direction due to movement of the wearer, a contractile force of the end sheet functions to hold the edges of the distal zones around the transverse middle of the crotch region and thereby effectively restrains movement of the distal zones. In this way, the distal zones are not significantly shifted away from the positions at which these distal zones come closer to or in contact with the wearer's inguinal region and both sides of the anus.

With the article including the pocket opening from the rear ends toward the longitudinal middle of the crotch region formed between the body-side surface and the end sheet, feces discharged in the article is reliably received in the pocket and the end sheet prevents feces from moving rearward in the longitudinal direction and leaking beyond the rear waist region.

The same effect is achieved also by the wearing article exploited so that the respective barrier sheets have inner surfaces of the front and rear ends bonded to the body-side surface with the front ends folded outward in the transverse direction and with inner edges of the rear ends directed inward in the transverse direction. Specifically, this unique arrangement allows the dimension by that the edges of the distal zones of the respective barrier sheets are spaced from each other to be gradually enlarged from the side of the rear waist region toward the side of the front waist region and thereby eliminates an anxiety that urination might occur outside the distal zones of the respective barrier sheets. In addition, these distal zones prevent the discharged urine from moving sideways and leaking beyond the opposed lateral margins of the article.

DETAILED DESCRIPTION OF THE PREFERRED EMBODIMENTS

Details of a disposable wearing article according to the present invention will be more fully understood from the description given hereunder with reference to the accompanying drawings.

Figure 1:
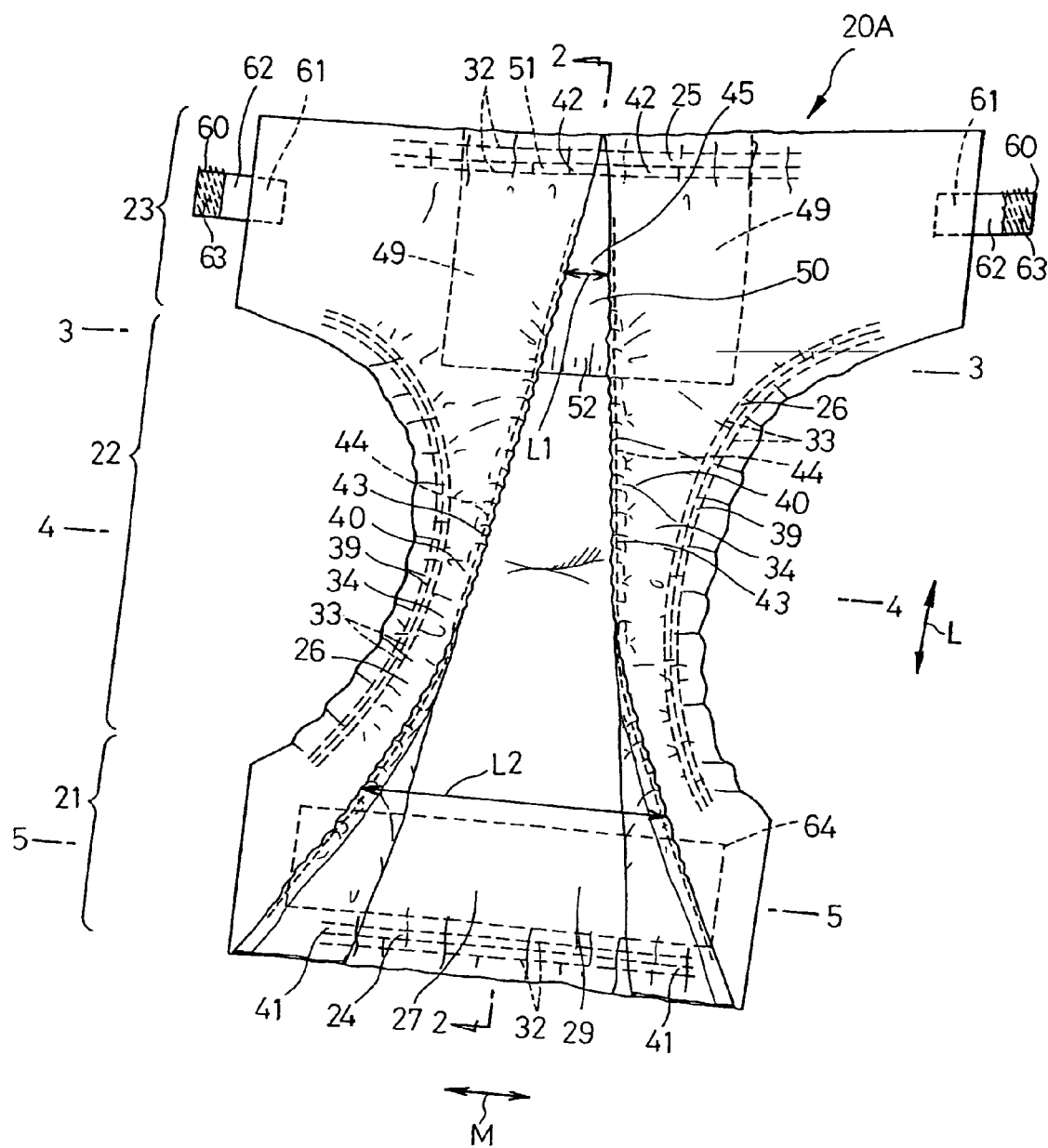
FIG. 1 is a perspective view showing a first embodiment of a wearing article according to the invention.
Figure 2:
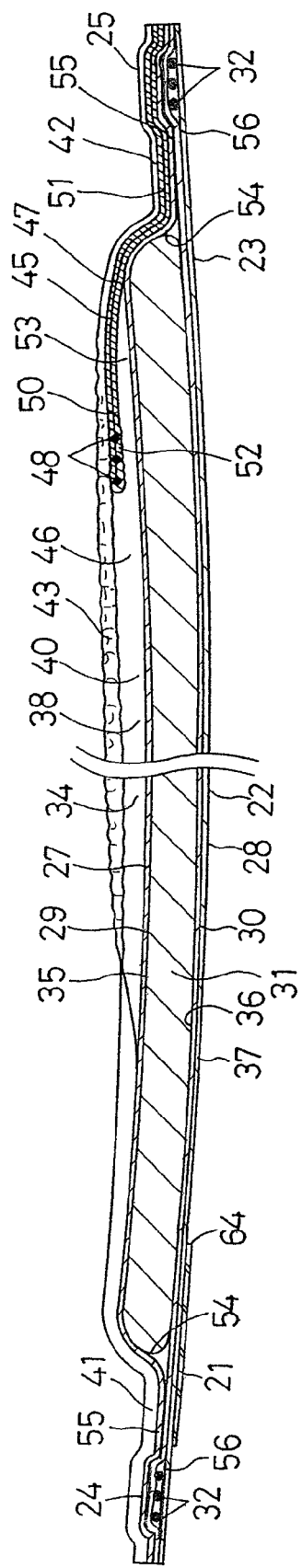
FIG. 2 is a sectional view taken along the line 2-2 in FIG. 1 with a crotch region partially cutaway.
Figure 3:
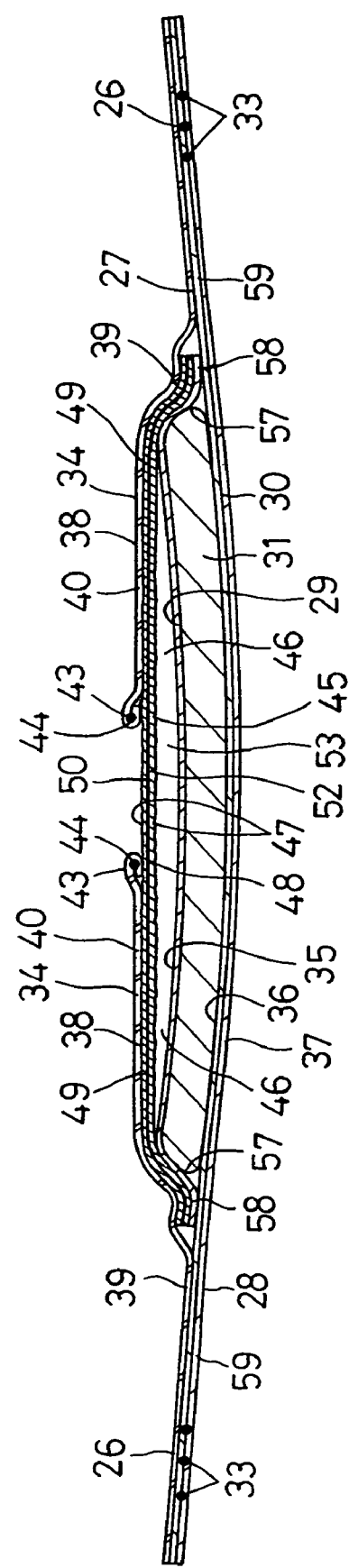
FIG. 3 is a sectional view taken along the line 3-3 in FIG. 1.
Figure 4:
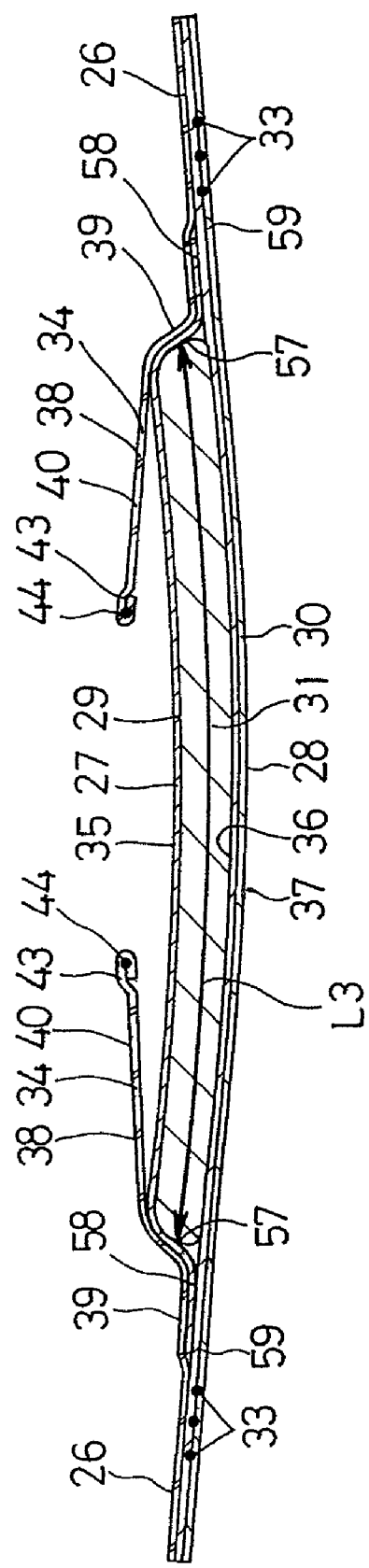
FIG. 4 is a sectional view taken along the line 4-4 in FIG. 1.
Figure 5:
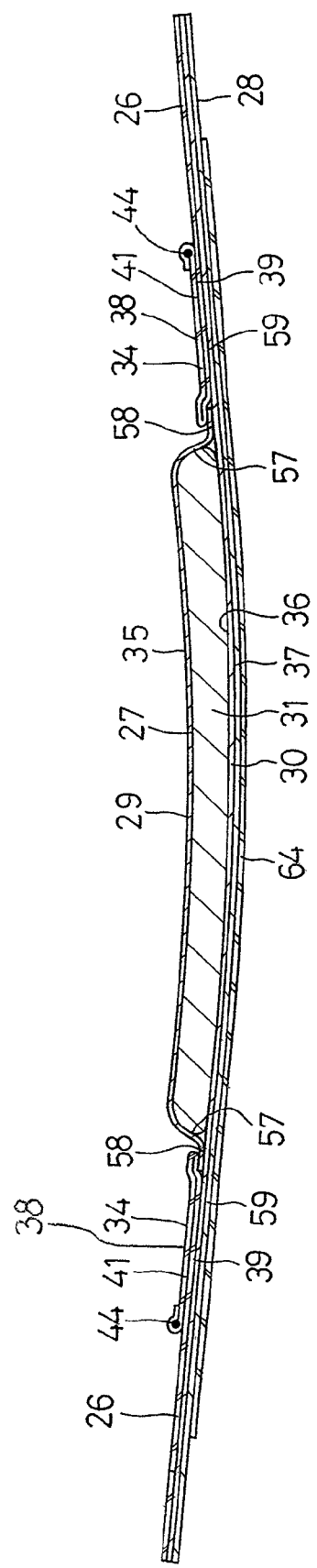
FIG. 5 is a sectional view taken along the line 5-5 in FIG. 1.

FIG. 1 is a perspective view showing a wearing article 20A according to a first embodiment of the invention, FIG. 2 is a sectional view taken along a line 2-2 in FIG. 1 with a crotch region partially cutaway, FIGS. 3 and 4 are sectional views taken along lines 3-3 and 4-4, respectively, in FIG. 1. FIG. 5 is a sectional view taken along the line 5-5 in FIG. 1. In FIG. 1, a transverse direction is indicated by an arrow M and a longitudinal direction is indicated by an arrow L.

The article 20A has, as viewed in the longitudinal direction, a front waist region 21, a rear waist region 23 and a crotch region 22 extending between these waist regions 21, 23. The article 20A is contoured by longitudinally opposite ends 24, 25 extending in the front and rear waist regions 21, 23, respectively, in the transverse direction and opposite lateral margins 26 extending in the longitudinal direction between the front waist region 21 and the rear waist region 23. The article 20A has a body-side surface 27 destined to come in contact with the wearer's skin and a garment-side surface 28 destined to face away from the wearer's skin. The article 20A comprises a liquid-pervious topsheet 29 defining the body-side surface 27, a liquid-impervious backsheet 30 defining the garment-side surface 28 and a liquid-absorbent core 31 sandwiched between these sheets 29, 30 (i.e., between the body-side surface 27 and the garment-side surface 28) so as to extend over the front waist region 21, the crotch region 22 and the rear waist region 23. The opposite lateral margins 26 of the crotch region 22 describe circular arcs which are convex inward in the transverse direction. The article 20A has a generally hourglass-like planar shape as will be apparent from FIG. 1. This article 20A is of open-type having the front and rear waist regions 21, 23 not connected with each other until the article 20 is put on the wearer's body.

A plurality of waist elastic members 32 extending in the transverse direction are attached to the longitudinally opposite ends 24, 25, respectively, in stretchable and contractible manner. A plurality of leg elastic members 33 extending in the longitudinal direction are attached to the opposite lateral margins 26 in stretchable and contractible manner. The lateral margins 26 are provided also with a pair of liquid-barrier sheets 34 opposed to and spaced from each other in the transverse direction and extending between the front and rear waist regions 21, 23. As a stock material for the topsheet 29, a hydrophilic fibrous nonwoven fabric 35 is used. As a stock material for the backsheet 30, a composite nonwoven fabric consisting of two hydrophobic fibrous nonwoven fabric layers 36, 37 laminated together. The core 31 comprises a mixture of particulate or fibrous super-absorbent polymers and fluff pulp fibers or a mixture of particulate or fibrous super-absorbent polymers, fluff pulp fibers and thermoplastic synthetic resin fibers, in any case, compressed to a desired thickness. Consequentially, the core 31 has a rigidity higher than those of the top- and backsheets 29, 30. The core 31 is covered in its entirety with a tissue paper (not shown) in order to prevent the core 31 from getting out of its initial shape and/or to prevent the polymers from partially falling off. The core 31 is bonded by the intermediary of the tissue paper to respective inner surfaces of the top- and backsheets 29, 30. The polymers may be selected from the group consisting of a starch- or cellulose-based polymer or synthetic polymer. An outer surface of the topsheet 29 and an outer surface of the barrier sheets 34 define the body-side surface 27 while an outer surface of the backsheet 30 defines the garment-side surface 28.

As a stock material for the barrier sheets 34, a hydrophobic fibrous nonwoven fabric 38 is used. Each of the barrier sheets 34 comprises a proximal zone 39 lying on each of the opposite lateral margins 26 and extending in the longitudinal direction, an elasticized distal zone 40 extending in the longitudinal direction and normally biased to rise up above the outer surface (i.e., the body-side surface 27) of the topsheet 29, front and rear ends 41, 42 lying on the ends 24, 25 of the article 20A with inner surfaces of the ends 41, 42 bonded to the body-side surface 27. Distal edges 43 of the respective distal zones 40 are opposed to and spaced from each other by a predetermined dimension in the transverse direction and this dimension is gradually enlarged from the side of the rear ends 42 toward the side of the front ends 41. The outer surface (i.e., the body-side surface 27) of the topsheet 29 is partially exposed between the distal edges 43 and the area of this partially exposed topsheet 29 is gradually enlarged from the side of the rear ends 42 toward the front ends 41. The part of the topsheet 29 exposed between the distal edges 43 has a generally inverted triangular planar shape as viewed from the rear ends 42 toward the front ends 41. The front ends 41, 41 are spaced from each other by a predetermined dimension in the transverse direction. The rear ends 42, 42 are also spaced from each other in the transverse direction but by a relatively small dimension and come in contact with each other on the rearmost edges thereof.

Elastic members 44 extending in the longitudinal direction are attached to distal edges 43 of the respective distal zones 40 in stretchable and contractible manner. More specifically, these elastic members 44 are stretched at a predetermined ratio in the longitudinal direction and bonded in such stretched state to the nonwoven fabric 38. A rectangular liquid-resistant end sheet 45 (i.e., the elasticized end sheet) functioning to pull the distal zones 40 closer to each other in the transverse direction is bonded to the rear ends 42 as well as to segments of the respective distal zones 40 extending aside toward the rear ends 42. The elastic members 44 contract as the article 20A bows with the topsheet 29 inside and contraction of the elastic members 44 causes the distal zones 40 to rise on the outer surface of the topsheet 29. The distal zones 40 rising up above the topsheet 29 in this manner form barriers functioning to prevent urine and feces from moving sideways. Between the segments of the distal zones 40 extending aside toward the rear ends 42 and the topsheet 29, there is formed a feces receiving space 46 adapted to receive feces discharged in the article 20A.

The end sheet 45 is interposed between the distal zones 40 as well as between the rear ends 42 and extends in the transverse direction. The end sheet 45 comprises (a) a hydrophobic fibrous nonwoven fabric 47 and (b) a plurality of stretchable and contractible elastic members 48 bonded to the nonwoven fabric 47 in stretchable and contractible manner to define a transversely elasticized segments 52 of end sheet 45. The elastic members 48 extend in the transverse direction so as to lie between the distal zones 40. Specifically, the elastic members 48 are stretched at a predetermined ratio in the transverse direction and bonded to the nonwoven fabric 47 in such stretched state. The end sheet 45 has opposite lateral segments 49, an intermediate segment 50 extending between the opposite lateral segments 49 and left free from the topsheet 29 as well as from the barrier sheets 34 and an edge 51 extending between the rear ends 42. The opposite lateral segments 49 are bonded to the outer surface of the topsheet 29, the inner surface of the proximal zones 39 and the inner surfaces of the respective distal zones 40. The edge 51 is bonded to the outer surface of the topsheet 29 and the inner surfaces of the respective rear ends 42. The lateral segments 49 are bonded to the distal zones 40 while the end sheet 45 is stretched at a predetermined ratio in the transverse direction. A pocket 53 opening from the rear ends 42 toward a longitudinal middle of the crotch region 22 is formed between the topsheet 29 and the end sheet 45.

The longitudinally opposite ends 24, 25 respectively comprise respective ends 55, 56 of the top- and backsheets 29, 30 extending outward from longitudinally opposite ends 54 of the core 31 and the longitudinally opposite ends 41, 42 of the respective barrier sheets 34. Along the respective ends 24, 25, the ends 55, 56 of the top- and backsheets 29, 30 are put flat together and have respective inner surfaces bonded together.

The front ends 41 of the respective barrier sheets 34 are laid in the front waist region 21 and bonded to the outer surfaces of the respective proximal zones 39. The rear ends 42 of the respective barrier sheets 34 are laid in the rear waist region 23 and bonded to the outer surface of the end sheet 45. The waist elastic members 32 are sandwiched between the nonwoven fabric layers 36, 37 forming together the backsheet 30, stretched at a predetermined ratio in the transverse direction and bonded to these nonwoven fabric layers 36, 37 in such stretched state.

The opposite lateral margins 26 respectively comprise respective lateral margins 58, 59 of the top- and backsheets 29, 30 extending transversely outward from opposite side edges 57 of the core 31 and the proximal zones 39 of the respective barrier sheets 34. Along these lateral margins 26, the lateral margins 58 of the topsheet 29 extend transversely outward slightly beyond the respective side edges 57 of the core 31 and the respective lateral margins 59 of the backsheet 30 as well as the proximal zones 39 of the respective barrier sheets 34 extend further transversely outward beyond the lateral margins 58. Along the lateral margins 26, the lateral margins 58, 59 of the top- and backsheets 29, 30 are put flat together with the proximal zones 39 of the respective barrier sheets 34, the top- and backsheets 29, 30 have respective inner surfaces bonded to each other, and inner and outer surfaces of the top- and backsheets 29, 30, respectively, are bonded to the inner surfaces of the respective barrier sheets 34. The leg elastic members 33 are sandwiched between the nonwoven fabric layers 36, 37 forming together the backsheet 30, stretched at a predetermined ratio in the longitudinal direction and bonded to these nonwoven fabric layers 36, 37 in such stretched state.

Tape fasteners 60 made of a plastic film are attached to the opposite lateral margins 26 of the rear waist region 23. Each of the tape fasteners 60 has a fixed section 61 and a free section 62 both extending in the transverse direction. The fixed section 61 is sandwiched between the lateral margin 59 of the backsheet 30 and the proximal zone 39 of the barrier sheet 34 and bonded to the respective inner surface of these sheets 30, 34. A male mechanical fastener 63 having a plurality of hooks is attached to the inner surface of the free section 62. Alternatively, the inner surface of the free section 62 may be coated with a pressure-sensitive adhesive instead of the male mechanical fastener 63 attached thereto.

The front waist region 21 is provided with a target tape 64 on which the free section 62 of the tape fastener 60 is detachably anchored. The target tape 64 takes the form of a female mechanical fastener 65 comprising a base and a plurality of loops protruding from the base. The target tape 64 is permanently bonded to the outer surface of the backsheet 30. When the free section 62 of the tape fastener 60 is coated with a pressure-sensitive adhesive, a plastic film may be used as the target tape 64.

Figure 6:
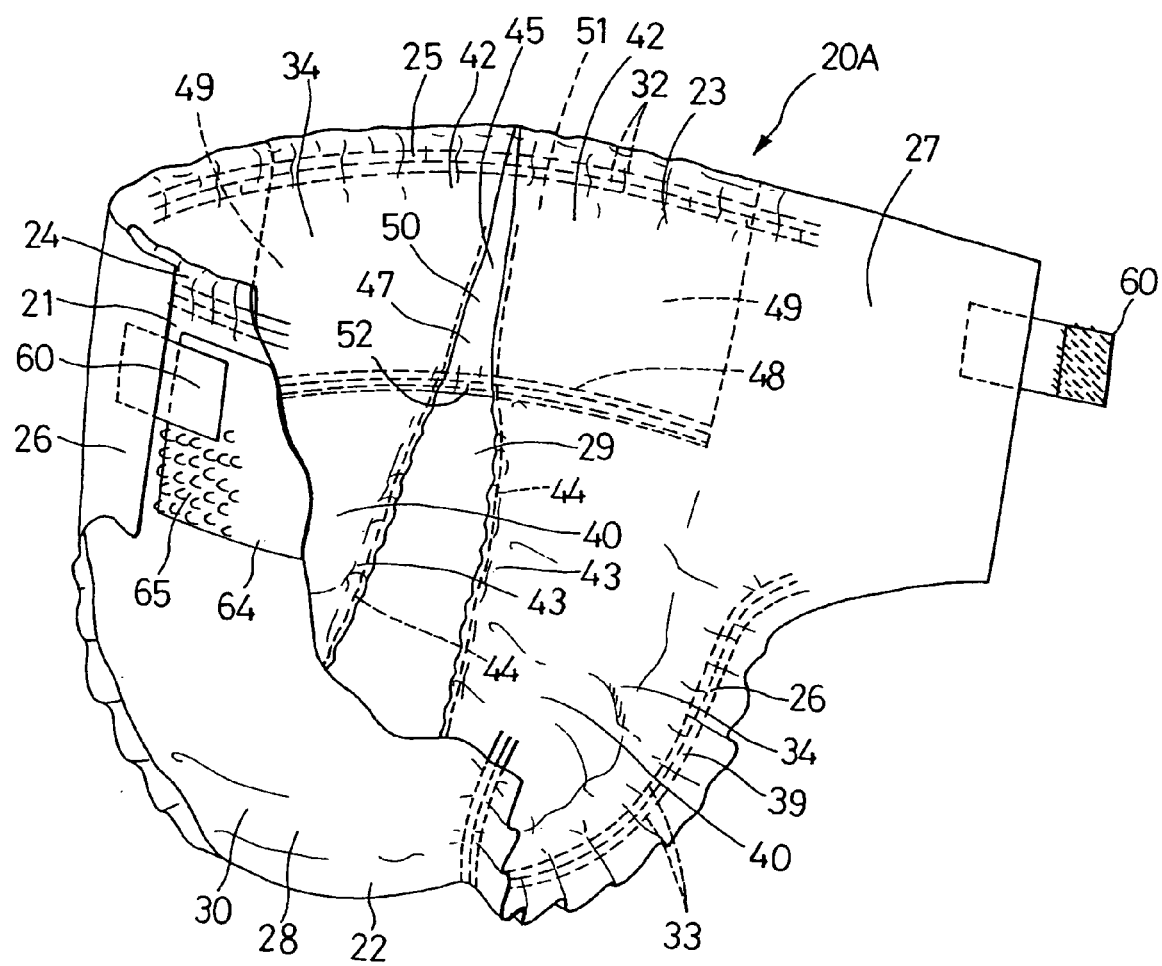
FIG. 6 is a partially cutaway perspective view showing the article in the course of being put on the wearer's body as viewed from the side of the front waist region.
Figure 7:
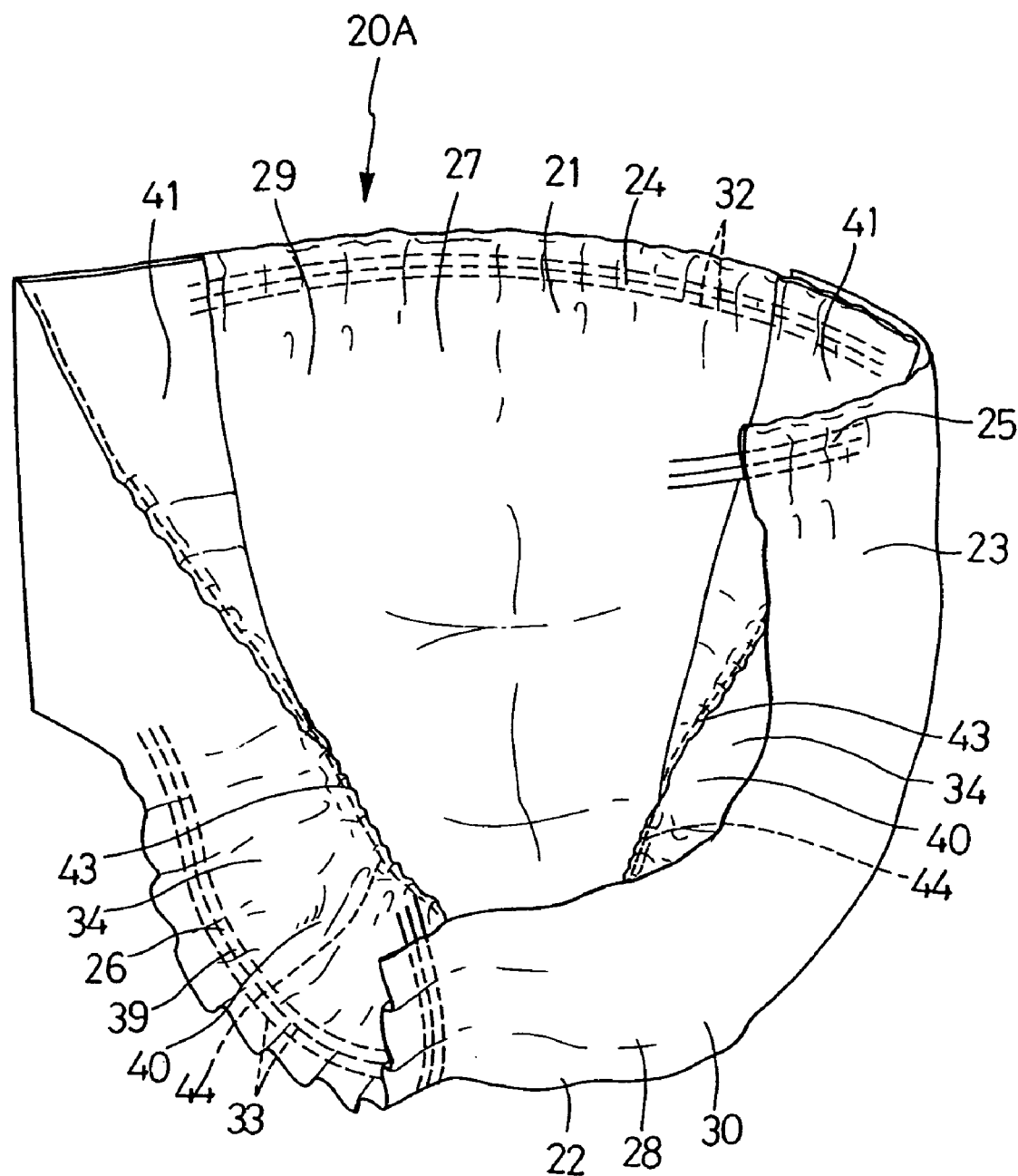
FIG. 7 is a partially cutaway perspective view showing the article in the course of being put on the wearer's body as viewed from the side of the rear waist region.
Figure 8:
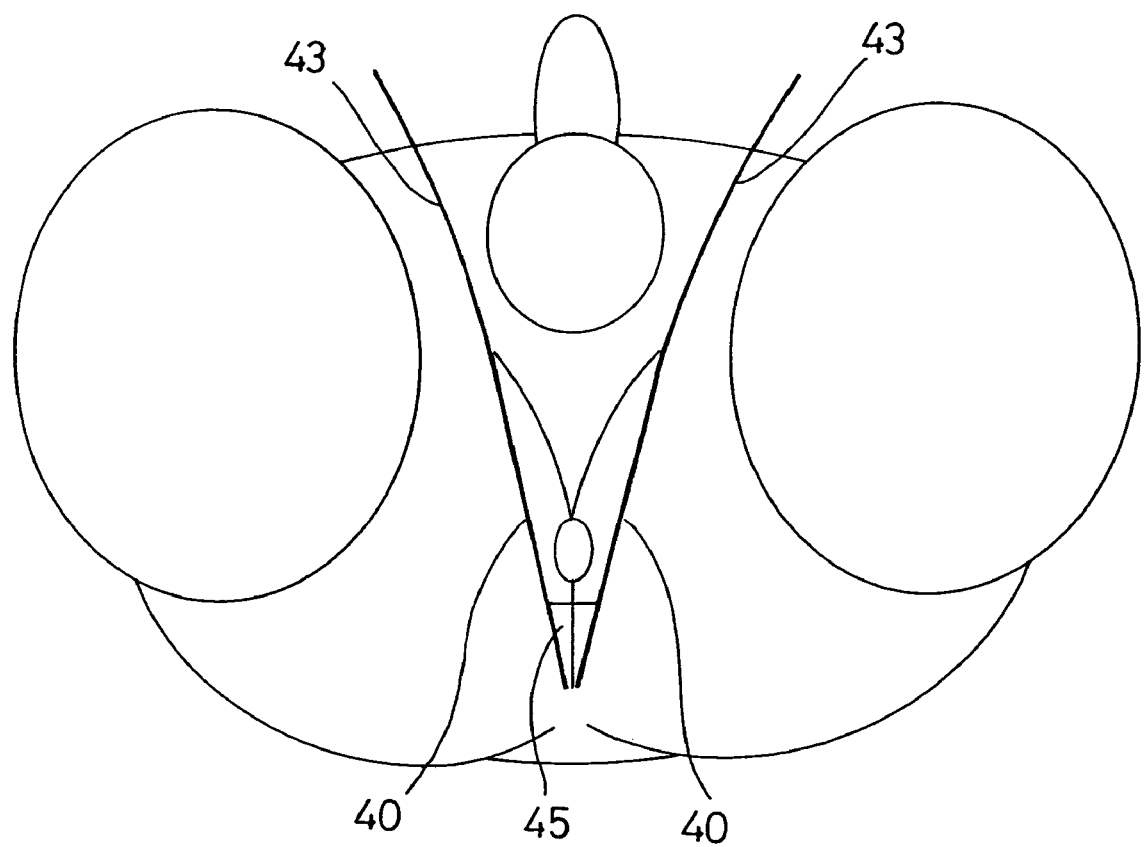
FIG. 8 is a schematic diagram illustrating positions of edges of respective distal zones in the article put on the wearer's body.
Figure 9:
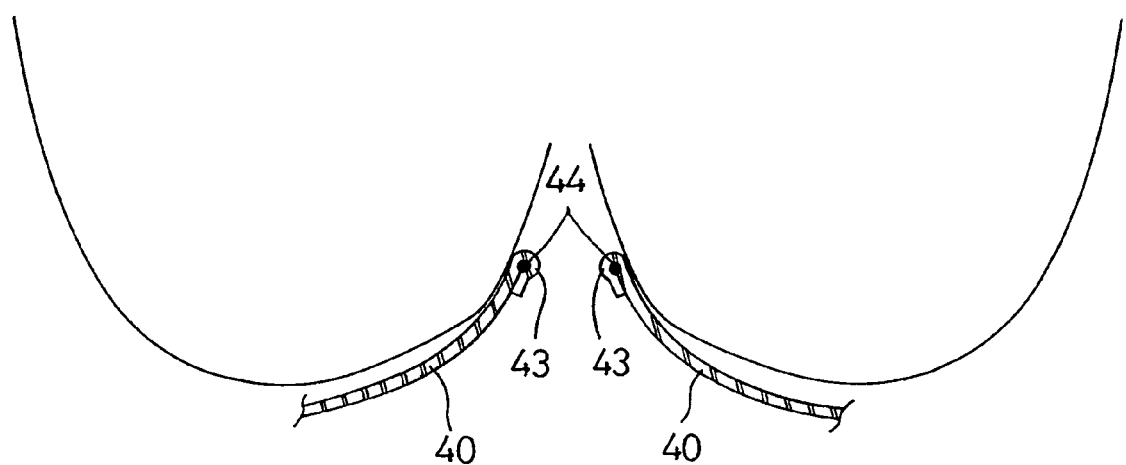
FIG. 9 is a schematic diagram illustrating positions the edges of the respective distal zones in the article put on the wearer's body.

FIGS. 6 and 7 are partially cutaway perspective views showing the article 20A in the course of being put on the wearer's body as viewed from the side of the front waist region 21 and as viewed from the side of the rear waist region 23, respectively. FIGS. 8 and 9 are schematic diagrams illustrating positions of the distal edges 43 of the distal zones 40 in the article 20A put on the wearer's body. Specifically, FIG. 8 illustrates the wearer's crotch region as viewed from below and FIG. 9 illustrates the wearer as viewed from the side of the buttock. The article 20A may be put on the wearer's body in accordance with, for example, steps of a procedure as follow: The wearer's buttock is placed on the body-side surface 27 of the crotch region 22 which is, in turn, folded onto the wearer's abdominal region. Then the transversely opposite lateral margins 26 of the rear waist region 23 are folded toward the wearer's abdominal region and placed on the respective outer sides of the transversely opposite lateral margins 26 of the front waist region 21. Thereupon, the free sections 62 of the respective tape fasteners 60 are anchored on the target tape 64 to connect the rear waist region 23 with the front waist region 21. A waist-hole and a pair of leg-holes are formed (not shown) as the front and rear waist regions 21, 23 are connected with each other in this manner.

With the article 20A put on the wearer's body, the distal edges 43 of the distal zones 40 of the respective barrier sheets 34, in the crotch region 22, come close to or in contact with the wearer's inguinal region and the distal edges 43 of the distal zones 40 extending from the crotch region 22 into the rear waist region 23 further go into the wearer's buttock cleavage so as to come close to or in contact with both sides of the anus. With the article 20A put on the wearer's body, feces discharged therein is received in the feces receiving space 46 and the pocket 53 through a clearance defined between the distal edges 43 of the respective distal zones 40. Feces received in this manner are covered from above with the distal zones 40 and the end sheet 45. Urine discharged between the distal edges 43 of the distal zones 40 is absorbed and contained by the core 31 after permeation through the topsheet 29.

The dimension by which the distal edges 43 of the distal zones 40 are spaced from each other is gradually reduced from the side of the crotch region 22 toward the side of the rear waist region 23, the feces receiving space 46 is formed between the topsheet 29 and the distal zones 40 of the respective barrier sheets 34 while the pocket 53 is formed between the topsheet 29 and the end sheet 45. With the article 20A constructed in this manner, feces discharged in the article 20A are received in the space 46 and the pocket 53, and the distal zones 40 of the respective barrier sheets 34 extending in the crotch region 22 and the rear waist region 23 cooperate with the end sheet 45 to cover feces received in the space 46 and the pocket 53 reliably from above. With the article 20A put on the wearer's body, feces discharged therein are practically not exposed between the distal zones 40 and there is substantially no anxiety that feces discharged in the article 20A might come in contact with the wearer's inguinal region and buttock. Thus the wearer's skin can be protected from soil with feces. In the article 20A put on the wearer's body, the distal zones 40 of the respective barrier sheets 34 prevent urine as well as feces from moving sideways and leaking beyond the opposite lateral margins 26 of the article 20A while the end sheet 45 prevents feces from moving in the longitudinal direction and leaking beyond the rear waist region 23.

The end sheet 45 including the transversely elasticized segment 52 is attached to the distal zones 40 in stretchable and contractible manner. Even if movement of the wearer biases the distal zones 40 extending aside toward the side of the rear ends 42 to move in the transverse direction, contractile force of the end sheet 45 functions to hold the distal edges 43 around the transverse middle of the crotch region 22 and thereby to restrain movement of the distal zones 40. With the article 20A put on the wearer's body, it is thus ensured that movement of the distal zones 40 is restrained by contractile force of the end sheet 45. With the article 20A put on the wearer's body, there is no anxiety that the distal zones 40 extending aside toward the side of the rear ends 42 might be significantly moved. Consequentially, the distal edges 43 of the distal zones 40 are kept closer to or in contact with the wearer's inguinal region and both sides of the anus and it is ensured that feces discharged in the article 20A are received in the feces receiving space 46 and the pocket 53 through the clearance defined between the distal edges 43 of the distal zones 40.

The minimum dimension L1 (See FIG. 1) by which the distal edges 43 of the respective distal zones 40 extending aside toward the side of the fixed rear ends 42 are spaced from each other is in a range of 0 to 25%, preferably 0 to 10%, more preferably 0 to 5% of the minimum transverse dimension L3 (See FIG. 4) of the core 31 extending in the crotch region 22. If the minimum dimension L1 by which the distal edges 43 are spaced from each other exceeds 25% of the minimum transverse dimension L3 of the core 31, it will be difficult for the distal zones 40 to cover feces sufficiently from above. As a result, feces will be exposed between the distal zones 40 and feces may cling to the wearer's inguinal region and buttock to contaminate the wearer's skin over a wide extent. The maximum dimension L2 (See FIG. 1) by which the distal edges 43 of the distal zones 40 extending aside toward the side of the front ends 41 is in a range of 26 to 120%, preferably 30 to 80% of the minimum transverse dimension L3 (See FIG. 4) of the core 31 extending in the crotch region 22. If the maximum dimension L2 by which the distal edges 43 are spaced from each other is less than 26% of the minimum transverse dimension L3, the dimension by which the distal edges 43 are spaced from each other will be insufficient to prevent discharge of urine from occurring outside the distal zones 40.

So far as the article 20A for baby is concerned, the minimum transverse dimension L3 of the core 31 extending in the crotch region 22 is in a range of about 5 cm to about 9 cm, the minimum dimension L1 by which the distal edges 43 are spaced from each other in the rear waist region 23 is in a range of 0 to 2.25 cm, preferably 0 to 0.9 cm, more preferably 0 to 0.45 cm and the maximum dimension L2 by which the distal edges 43 are spaced from each other in the front waist region 21 is in a range of 1.3 to 10.8 cm, preferably 1.5 to 7.2 cm. In the case of the article 20A for adult, the minimum transverse dimension L3 of the core 31 extending in the crotch region 22 is in a range of about 12 to about 25 cm, the minimum dimension L1 by which the distal edges 43 are spaced from each other in the rear waist region 23 is in a range of 0 to 6.25 cm, preferably 0 to 2.5 cm, more preferably 0 to 1.25 cm and the maximum dimension L2 by which the distal edges 43 are spaced from each other in the front waist region 21 is in a range of 3.12 to 30 cm, preferably 3.6 to 20 cm.

Figure 10:
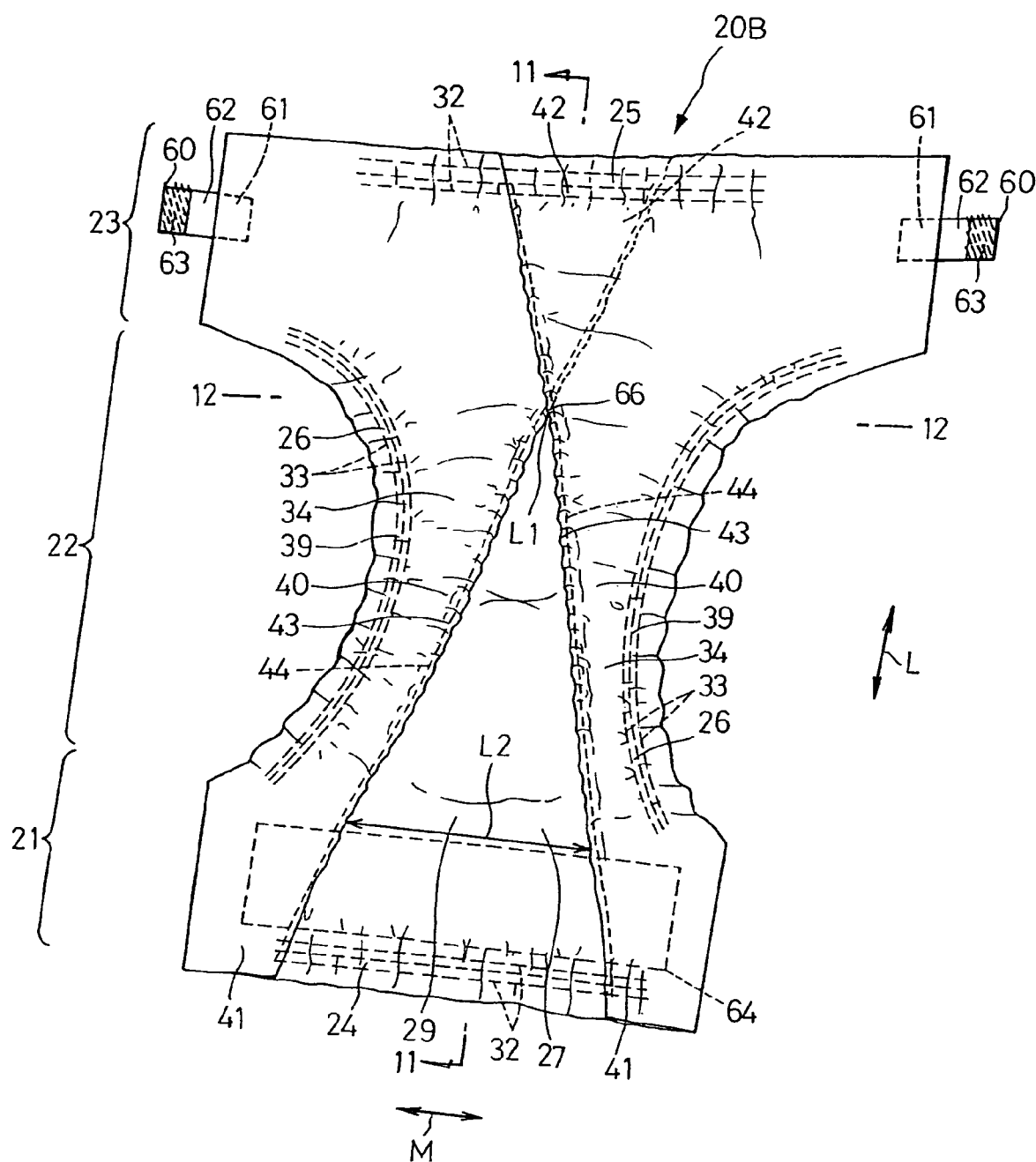
FIG. 10 is a perspective view showing the wearing article according to a second embodiment of the invention.
Figure 11:
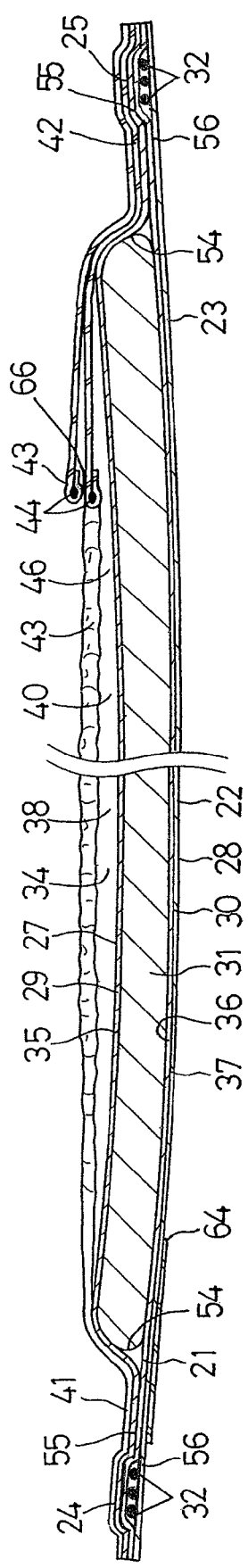
FIG. 11 is a sectional view taken along the line 11-11 in FIG. 10 with a crotch region partially cutaway.
Figure 12:
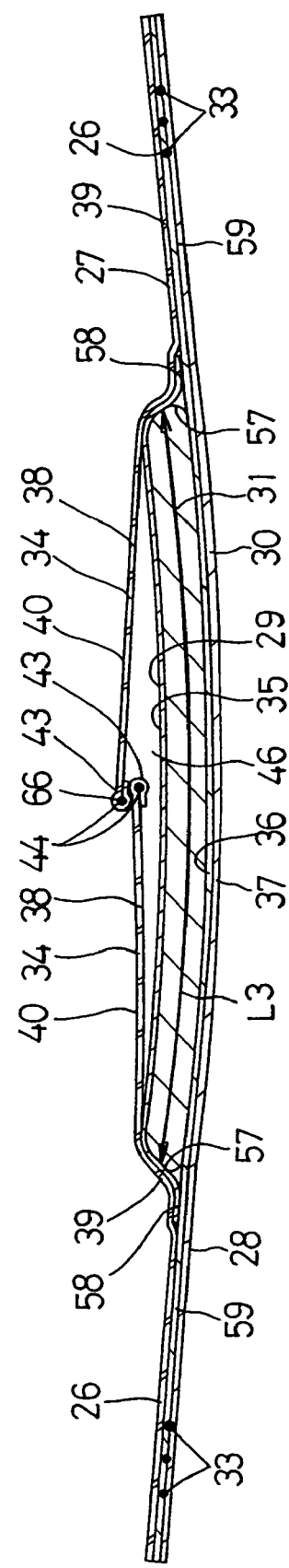
FIG. 12 is a sectional view taken along the line 12-12 in FIG. 10.

FIG. 10 is a perspective views showing a wearing article 20B according to a second embodiment of the invention, FIG. 11 is a sectional view taken along the line 11-11 in FIG. 10 with the crotch region 22 partially cutaway and FIG. 12 is a sectional view taken along the line 12-12 in FIG. 10. In FIG. 10, a longitudinal direction is indicated by an arrow L and a transverse direction is indicated by an arrow M. The article 20B is similar to the article 20A shown in FIG. 1 except that the distal zones 40 of the respective barrier sheets 34 partially overlap each other, the rear ends 42 overlap each and the end sheet 45 is not provided. The remaining features the same to those in the article 20A of FIG. 1 are designated with similar reference numerals and detailed description thereof will be eliminated hereinafter.

In the rear waist region 23, the respective barrier sheets 34 have the rear ends 42 bonded so as to overlap each other in the transverse direction. Specifically, the inner surface of the one rear end 42 is put flat together with the outer surface of the other rear end 42 and bonded together in such state. In a section of the crotch region 22 extending aside toward the rear waist region 23 and in the rear waist region 23, the distal zones 40 extending aside toward the side of the rear ends 42 intersect with each other in the transverse direction and the inner surface of the distal zone 40 is put flat together with the outer surface of the other distal zone 40. The elastic members 44 attached to the distal edges 43 of the respective distal zones 40 intersect with each other in the crotch region 22. With the article 20B put on the wearer's body, feces discharged therein is received in the feces receiving space 46 defined between the topsheet 29 and the distal zones 40 extending aside toward the side of the rear ends 42.

A dimension by which the distal edges 43 are spaced from each other in the transverse direction is gradually enlarged from an intersection 66 of the distal edges 43 toward the front ends 41. The segments of the distal zones 40 extending forward from the intersection 66 in the longitudinal direction rise up on the outer surface (i.e., the body-side surface 27) of the topsheet 29 to form barriers functioning to prevent urine and feces from moving sideways. Longitudinally forward from the intersection 66, the outer surface of the topsheet 29 is partially exposed between the distal edges 43 and the area of such exposed topsheet 29 is gradually enlarged from the intersection 66 toward the front waist region 21. The part of the topsheet 29 exposed between the distal edges 43 in this manner has a generally inverted triangular planar shape as viewed from the intersection 66 toward the front waist region 21. The front ends 41 are spaced from each other by a predetermined dimension in the transverse direction, with inner surfaces of the front ends 41 bonded to the outer surface of the topsheet 29.

With the article 20B put on the wearer's body, the distal edges 43 of the distal zones 40 of the respective barrier sheets 34, in the crotch region 22, come close to or in contact with the wearer's inguinal region and the distal edges 43 of the distal zone 40 extending from the crotch region 22 into the rear waist region 23 further go into the wearer's buttock cleavage so as to come close to or in contact with both sides of the anus in the same manner as illustrated by FIGS. 8 and 9. With the article 20B put on the wearer's body, feces discharged therein are received in the feces receiving space 46 through a clearance defined between the distal edges 43 of the respective distal zones 40. Feces received in this manner are covered from above with the distal zones 40 extending aside toward the side of the rear ends 42. Urine discharged between the distal edges 43 of the distal zones 40 is absorbed and contained by the core 31 after permeation through the topsheet 29.

With the article 20B put on the wearer's body, feces discharged in the article 20B are received in the feces receiving space 46 and the distal zones 40 of the respective barrier sheets 34 extending in the crotch region 22 and the rear waist region 23 cover feces received in the space 46 from above. Consequentially, feces discharged therein are practically not exposed between the distal zones 40 and there is substantially no anxiety that feces discharged in the article 20B might come in contact with the wearer's inguinal region and buttock. Thus the wearer's skin can be protected from soil with feces, and the distal zones 40 of the respective barrier sheets 34 prevent urine as well as feces from moving sideways and leaking beyond the opposite lateral margins 26 of the article 20B. In the rear waist region 23, the distal zones 40 prevent feces from moving rearward in the longitudinal direction and leaking beyond the rear waist region 23.

The minimum dimension L1 (See FIG. 10) by which the distal edges 43 of the distal zones 40 extending aside toward the side of the rear ends 42 are spaced from each other corresponds to 0% of the minimum transverse dimension L3 (See FIG. 12) of the core 31 extending in the crotch region 22. The maximum dimension L2 (See FIG. 10) by which the distal edges 43 of the distal zones 40 extending aside toward the side of the front ends 41 is in a range of 26 to 120%, preferably 30 to 80% of the minimum transverse dimension L3 (See FIG. 12). So far as the article 20B for baby is concerned, specific values of the maximum dimension L2 by which the distal edges 43 are spaced from each other are the same as those having been described with reference to the article 20A of FIG. 1. Specific values of the maximum dimension L2 by which the distal edges 43 are spaced from each other in the article 20B for adult are also the same as those having been described with reference to the article 20A of FIG. 1.

Figure 13:
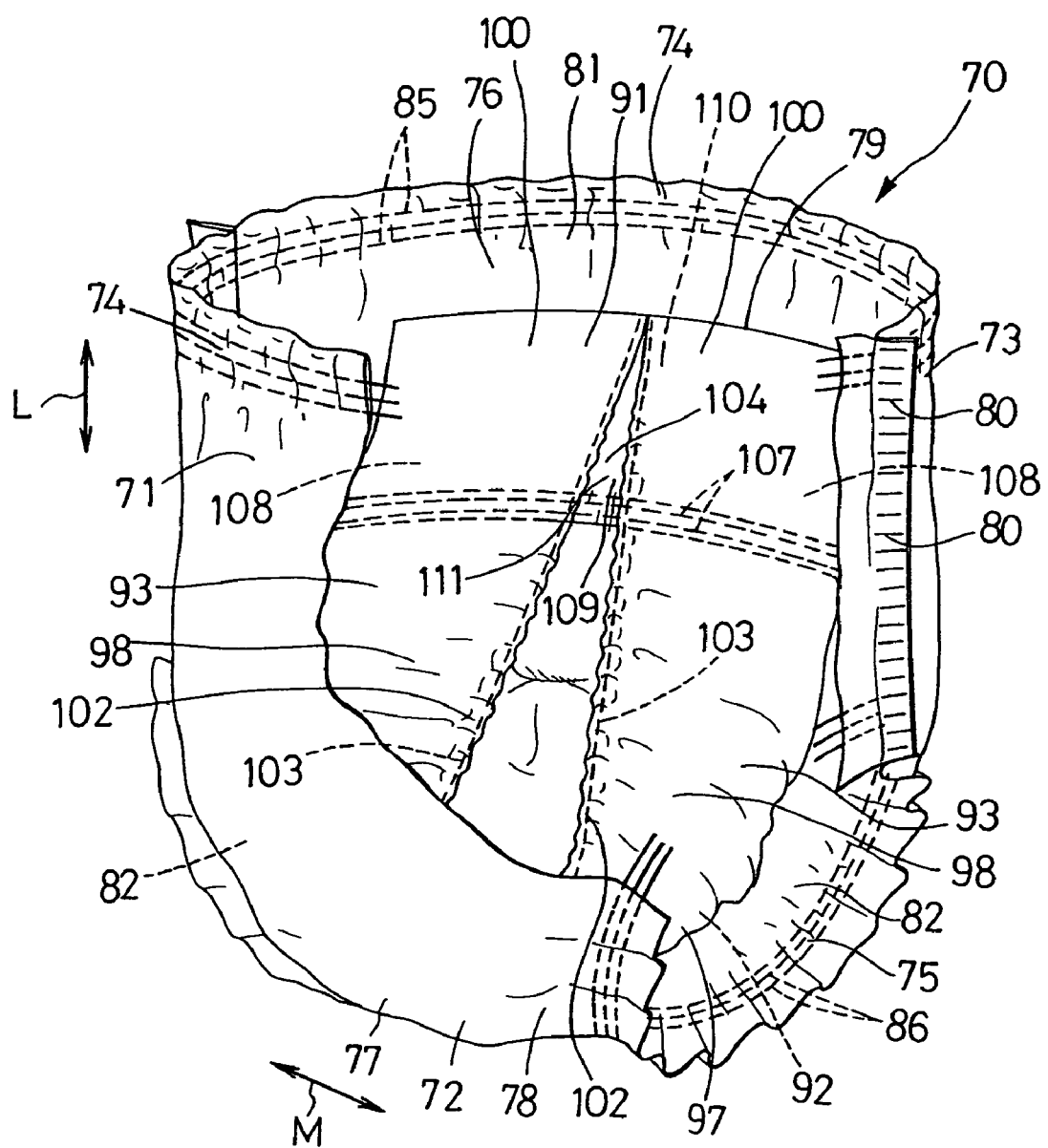
FIG. 13 is a partially cutaway perspective view showing the wearing article according to a third embodiment of the invention.
Figure 14:
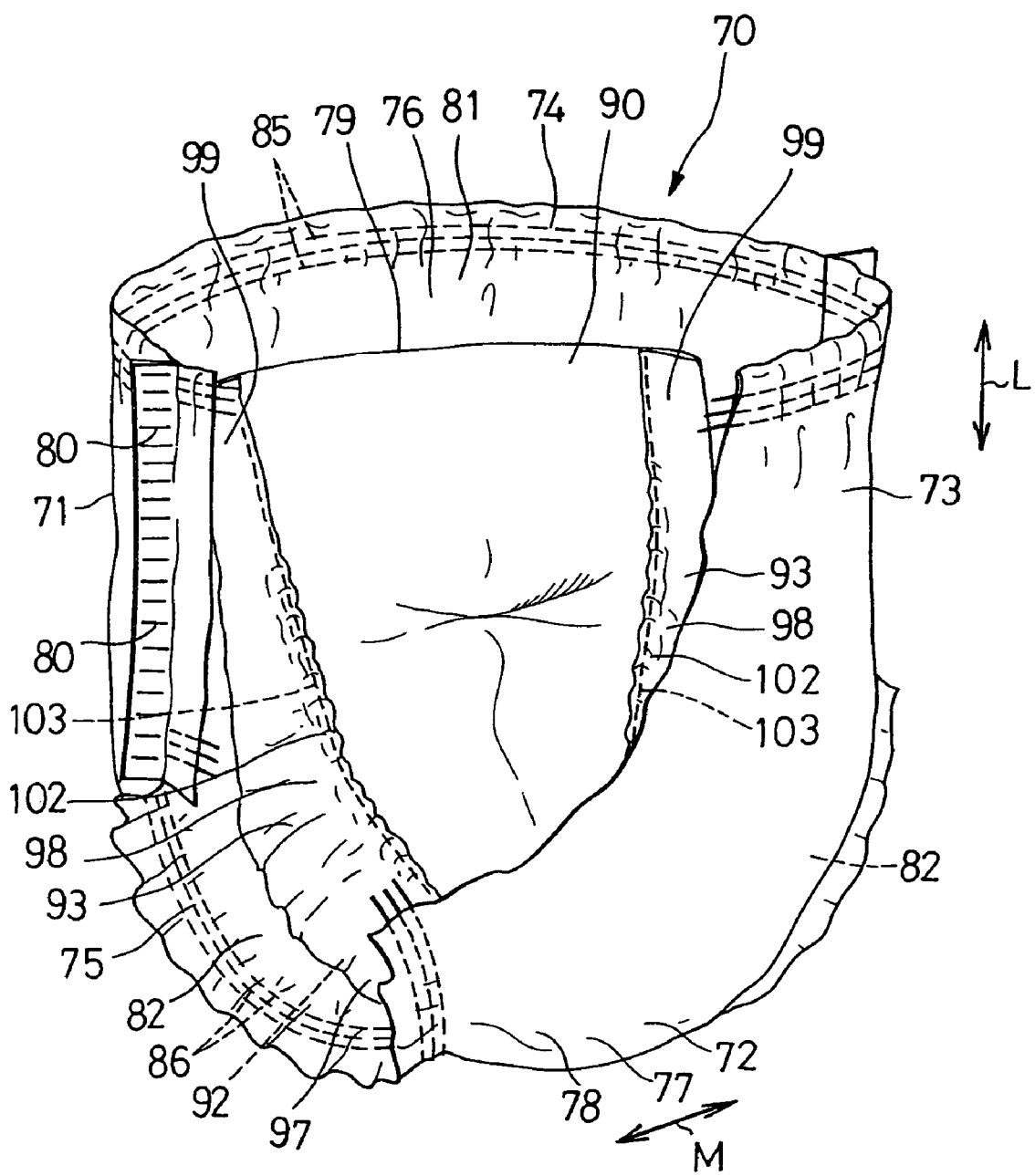
FIG. 14 is a partially cutaway perspective view showing the wearing article according to a fourth embodiment of the invention.
Figure 15:
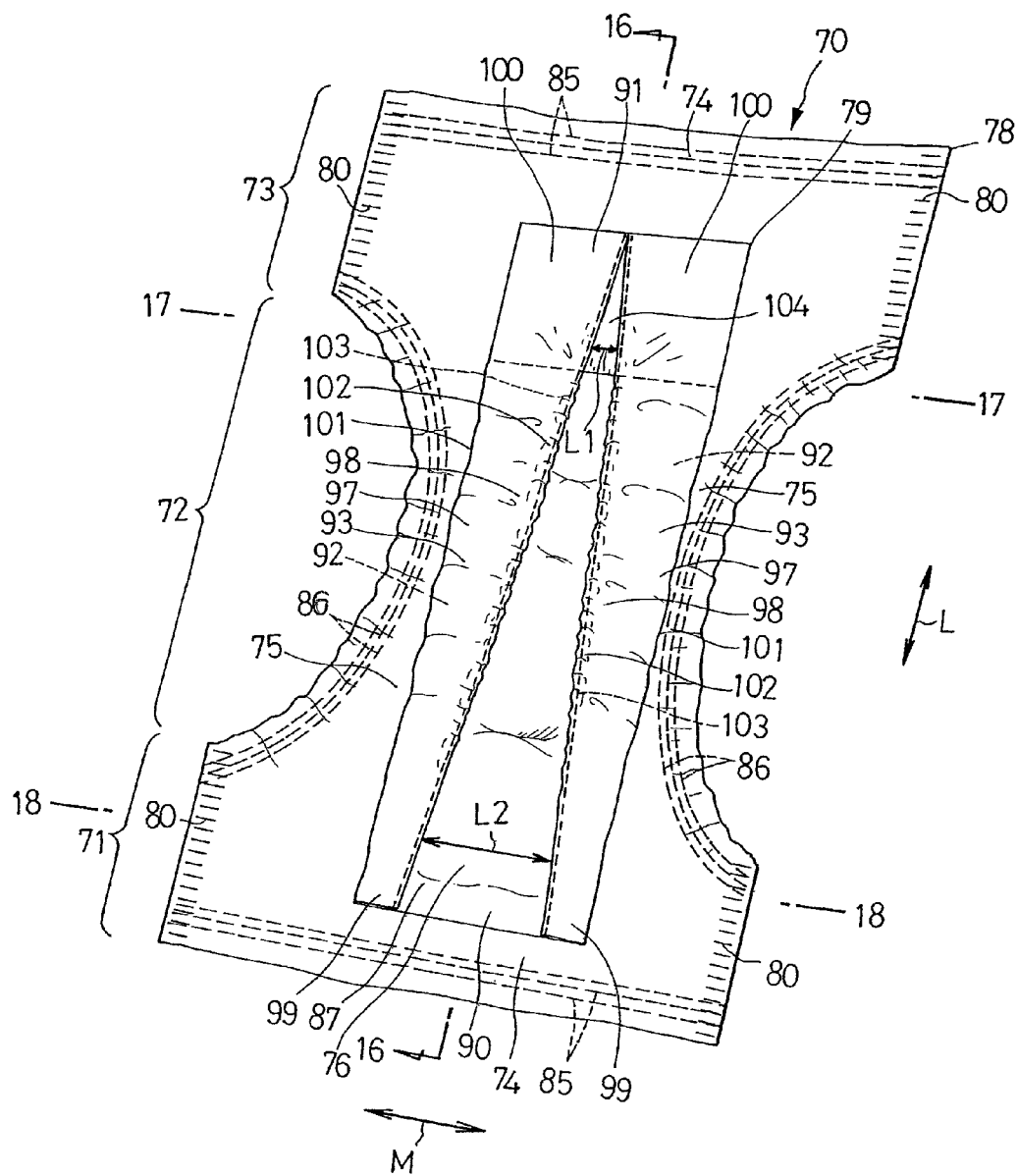
FIG. 15 is a developed perspective view showing the article of FIG. 13.

FIGS. 13 and 14 are partially cutaway perspective views showing a wearing article 70 according to third and fourth embodiments of the invention, respectively. FIG. 13 shows the article 70 as viewed from the side of a front waist region 71 and FIG. 14 shows the article 70 as viewed from the side of a rear waist region 73. FIG. 15 is a developed perspective view showing the article 70 with the front and rear waist regions 71, 73 disconnected from each other. In these figures, a transverse direction is indicated by an arrow M and a longitudinal direction is indicated by an arrow L.

The article 70 has a front waist region 71, a rear waist region 73 and a crotch region 72 extending between these waist regions 71, 73. The article 70 is contoured by longitudinally opposite ends 74 extending in the front and rear waist regions 71, 73, respectively, in the transverse direction and opposite lateral margins 75 extending in the longitudinal direction between the front and rear waist regions 71, 73. The article 70 has a body-side surface 76 destined to come in contact with the wearer's skin and a garment-side surface 77 destined to face away from the wearer's skin. The article 70 comprises a liquid-impervious first backsheet 78 defining a whole shape including the front and rear waist regions 71, 73 and the crotch region 72, and a laminated panel 79 attached to the inner surface of the backsheet 78. The opposite lateral margins 75 in the crotch region 72 describe circular arcs which are convex inward in the transverse direction. The article 70 has a generally hourglass-like planar shape as will be apparent from FIG. 15. In the article 70, the front and rear waist regions 71, 73 are put flat and bonded together along the opposite lateral margins 75 at a plurality of heat-sealing lines 80 arranged intermittently along these lateral margins 75. This article 70 is of pants-type or pull-on type having the front and rear waist regions 71, 73 previously connected with each other so as to form a waist-hole 81 and a pair of leg-holes 82 as will be apparent from FIGS. 13 and 14.

As a stock material for the backsheet 78, a composite nonwoven fabric consisting of two hydrophobic fibrous nonwoven fabric layers 83, 84 laminated together is used. A plurality of waist elastic members 85 extending in the transverse direction are attached to the longitudinally opposite ends 74, respectively, in stretchable and contractible manner. The waist elastic members 85 are sandwiched between the nonwoven fabric layers 83, 84, stretched at a predetermined ratio in the transverse direction and bonded to these nonwoven fabric layers 83, 84 in such stretched state. A plurality of leg elastic members 86 extending in the longitudinal direction are attached to the opposite lateral margins 75, respectively, in stretched state. The leg elastic members 86 are sandwiched between the nonwoven fabric layers 83, 84, stretched in a predetermined ratio in the longitudinal direction and bonded to these nonwoven fabric layers 83, 84 in such stretched state.

The panel 79 has a generally rectangular planar shape and occupies the crotch region 72 as well as parts or the front and rear waist regions 71, 73. The panel 79 comprises a liquid-pervious topsheet 87 lying on the body-side, a liquid-impervious second backsheet 88 lying on the garment-side and a liquid-absorbent core 89 sandwiched between the top- and backsheets 87, 88 (i.e., between the body-side surface 76 and the garment-side surface 77) so as to extend over the front and rear waist regions 71, 73 as well as the crotch region 72 as shown. The panel 89 has a pair of longitudinally opposite ends 90, 91 extending in the front and rear waist regions 71, 73 in the transverse direction and opposite lateral margins 92 extending in the longitudinal direction in coincidence with the opposite lateral margins 75. In the panel 79, the outer surface of the second backsheet 88 constituting the panel 79 is bonded to the inner surface of the first backsheet 78. A pair of liquid-resistant barrier sheets 93 spaced from and opposed to each other in the transverse direction and extending between the front and rear waist regions 71, 73 are attached to the opposite lateral margins (in coincidence with the opposite lateral margins 75 of the article 70).

As a stock material for the topsheet 87, a hydrophilic fibrous nonwoven fabric 94 is used. As a stock material for the backsheet 88, a breathable liquid-impervious oriented film 95 which contains therein fine particles of inorganic substance such as silica or alumina is used. The core 89 comprises the same mixture as the core 31 of the article 20A shown in FIG. 1 and entirely wrapped with a tissue paper (not shown). The core 89 is bonded to the inner surfaces of the top- and backsheets 87, 88, respectively, by the intermediary of the tissue paper. In the article 70, the inner surface of the backsheet 78, the outer surface of the topsheet 87 and the outer surfaces of the respective barrier sheets 93 define together the body-side surface 76 outside a peripheral edge of the panel 79 and the outer surface of the backsheet 78 defines the garment-side surface 77.

As a stock material for the barrier sheets 93, a hydrophobic fibrous nonwoven fabric 96 is used. Each of the barrier sheets 93 comprises a proximal zone 97 lying on each of the opposite lateral margins 92 and extending in the longitudinal direction, an elasticized distal zone 98 extending in the longitudinal direction and normally biased to rise up on the outer surface (i.e., the body-side surface 76) of the topsheet 87, and front and rear ends 99, 100 lying on longitudinally opposite ends 90, 91 of the panel 79 with inner surfaces of the ends 99, 100 bonded to the body side surface 76. A transverse dimension from the side edge 101 of the proximal zone 97 extending along the lateral margin 92 of the panel 79 to the distal edge 102 of the associated distal zone 98 is larger in the area extending aside toward the rear ends 100 than in the area extending aside toward the front ends 99. The distal edges 102 of the respective distal zones 98 are opposed to and spaced from each other by a predetermined dimension in the transverse direction and this dimension is gradually enlarged from the side of the rear ends 100 toward the side of the front ends 99. The outer surface (i.e., the body-side surface 76) of the topsheet 87 is partially exposed between the distal edges 102 and an area of such exposed topsheet 87 is gradually enlarged from the side of the rear ends 100 toward the front ends 99. The topsheet 87 exposed between the distal edges 102 in this manner has a generally inverted triangular shape as viewed from the rear ends 100 toward the front ends 99. The front ends 99 are spaced from each other in the transverse direction by a predetermined dimension. The rear ends 100 are slightly spaced from each other in the transverse direction and respective rear edges thereof are contiguous to each other.

Stretchable and contractible elastic members 103 extending in the longitudinal direction are attached to distal edges 102 of the respective distal zones 98 in stretchable and contractible manner. More specifically, these elastic members 103 are stretched at a predetermined ratio in the longitudinal direction and bonded in such stretched state to the distal edges 102 of the respective distal zones 98. A rectangular liquid-resistant end sheet 104 (i.e., elasticized end sheet) functioning to pull the distal zones 98 closer to each other is attached to the rear ends 100 as well as to the segments of the distal zones 98 extending aside toward the ends 100 in stretchable and contractible manner. In the barrier sheets 93, the elastic members 103 contract as the article 70 bows in the longitudinal direction with the topsheet 87 inside and thereby cause the distal zones 98 to rise up on the outer surface of the topsheet 87. In this way, the distal zones 98 form barriers functioning to prevent urine and/or feces from moving sideways. Base points at which the distal zones 98 rise are defined on the core 89 immediately inside opposite side edges 116 of the core 89. Between the segments of the distal zones 98 extending aside toward the rear ends 100 and the topsheet 78, a feces receiving space 105 adapted to receive feces discharged in the article 70 is formed.

The end sheet 104 is interposed between the distal zones 98 as well as between the rear ends 100 and extends in the transverse direction. The end sheet 104 comprises a hydrophobic fibrous nonwoven fabric 106 and a plurality of stretchable and contractible elastic members 107 bonded to the nonwoven fabric 106 in stretchable and contractible manner. The elastic members 107 extend in the transverse direction so as to lie between the distal zones 98. Specifically, the elastic members 107 are stretched at a predetermined ratio in the transverse direction and bonded to the nonwoven fabric 106 in such stretched state. The end sheet 104 comprises opposite lateral segments 108, an intermediate segment 109 extending between the opposite lateral segments 108 and left free from the topsheet 87 as well as from the barrier sheets 93 and an edge 110 extending between the rear ends 100. The opposite lateral segments 108 are bonded to the outer surface of the topsheet 87, the inner surfaces of the proximal zones 97 and the inner surfaces of the respective distal zones 98. The edge 110 is bonded to the outer surface of the topsheet 87 and the inner surfaces of the respective rear ends 100. The lateral segments 108 are bonded to the distal zones 98 while the end sheet 104 is stretched at a predetermined ratio in the transverse direction. Of the end sheet 104, a portion 111 of the intermediate segment 109 extending between the distal zones 98 is stretchable and contractible in the transverse direction. Between the topsheet 87 and the end sheet 104, a pocket 112 opening from the rear ends 42 toward a longitudinal middle of the crotch region 22 is formed.

Figure 16:
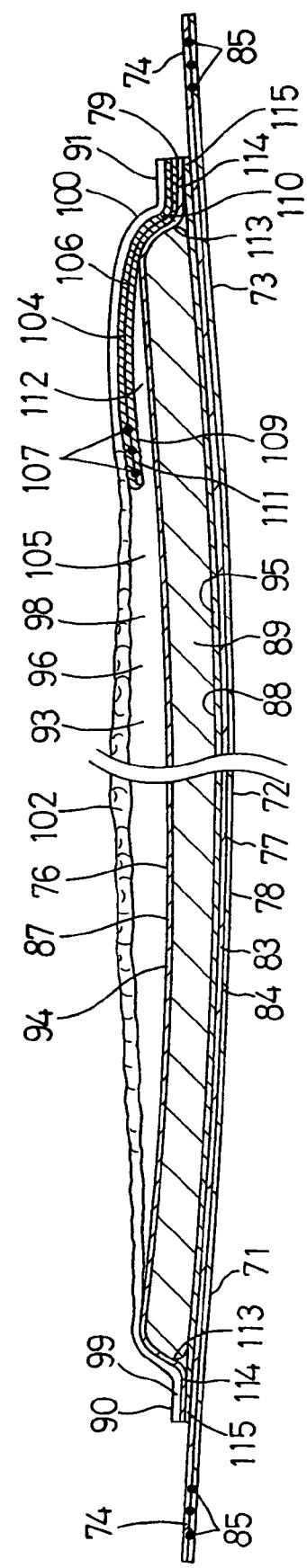
FIG. 16 is a sectional view taken along the line 16-16 in FIG. 14 with a crotch region partially cutaway.
Figure 17:
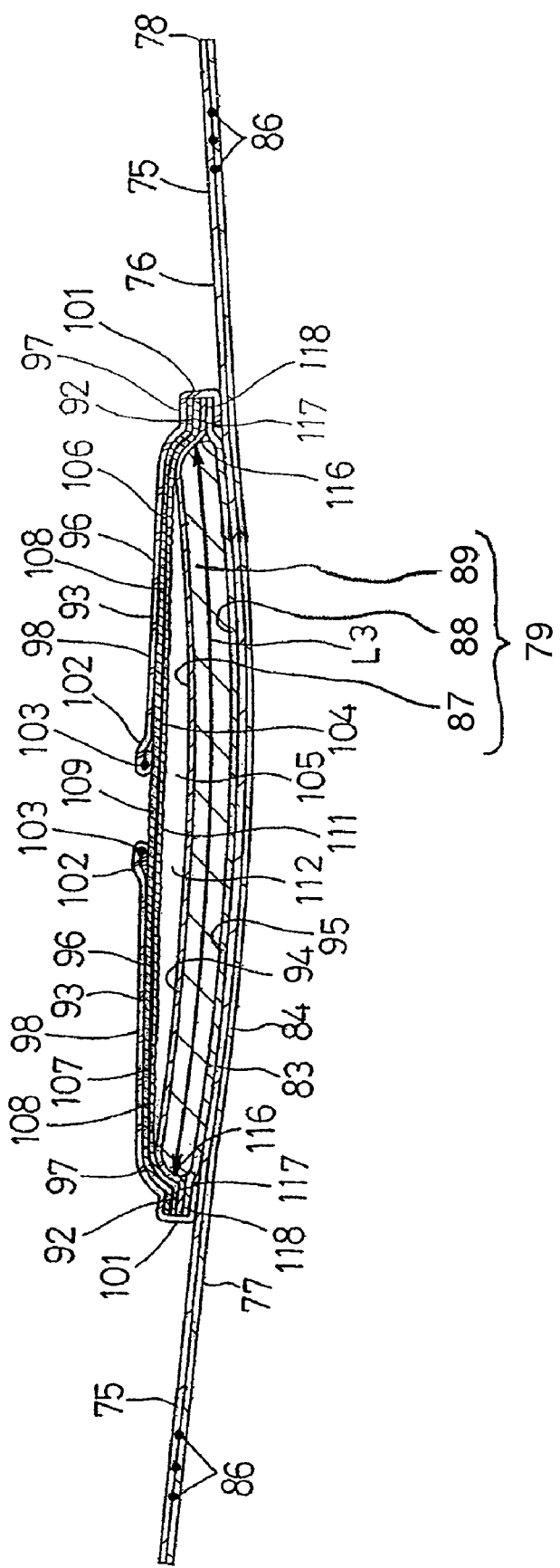
FIG. 17 is a sectional view taken along the line 17-17 in FIG. 14.
Figure 18:
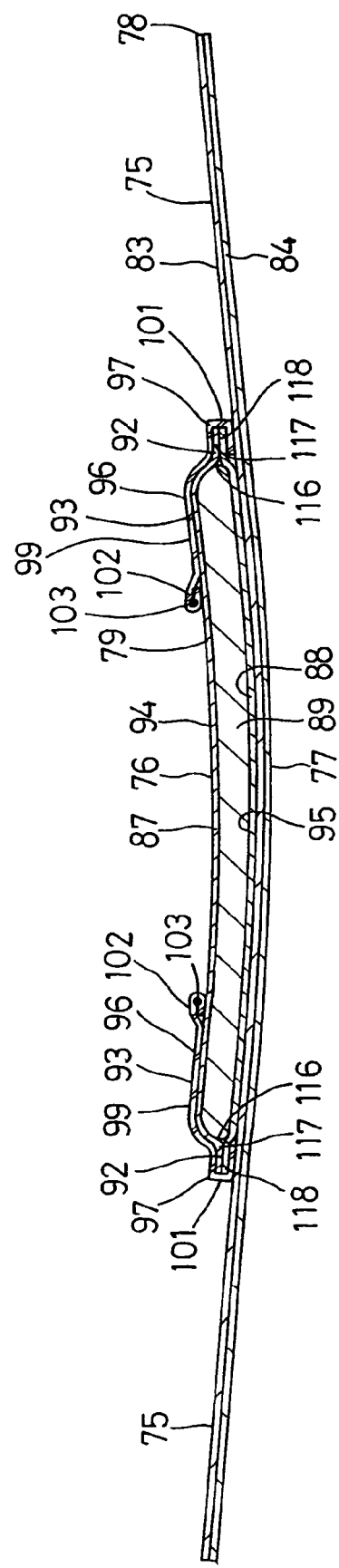
FIG. 18 is a sectional view taken along the line 18-18 in FIG. 14.

FIGS. 16 and 17 are sectional views taken along lines 16-16 and 17-17 in FIG. 15, respectively, with the crotch region 72 partially cutaway, and FIG. 18 is a sectional view taken along the line 18-18 in FIG. 14. The longitudinally opposite ends 90, 91 of the panel 79 are respectively formed by the ends 114, 115 of the top- and backsheets 87, 88 and the ends 99, 100 of the respective barrier sheets 93 extending outward in the longitudinal direction beyond the longitudinally opposite ends 113 of the core 89. Along the ends 90, 91, the ends 114, 115 of the top- and backsheets 87, 88 are put flat together and respective inner surfaces of these sheets 87, 88 are bonded to each other. The front ends 99 of the respective barrier sheets 93 are laid along the end 90 (i.e., the front waist region 71 of the article 70) of the panel 79 and bonded to the outer surface of the topsheet 87. The rear ends 100 of the respective barrier sheets 93 are laid along the end 91 (i.e., the rear waist region 73 of the article 70) of the panel 79 and bonded to the end sheet 104.

The opposite side edges 92 of the panel 79 are respectively formed by the respective lateral margins 117, 118 of the top- and backsheets 87, 88 and the proximal zones 97 of the respective barrier sheets 93 extending transversely outward beyond the opposite side edges 116 of the core 89. Along these side edges 92, the lateral margins 117, 118 of the top- and backsheets 87, 88, respectively, are put flat together with the proximal zones 97 of the respective barrier sheets 93 and the top- and backsheets 87, 88 have the respective inner surfaces bonded to each other. In addition, the outer surface of the topsheet 87 is bonded to the inner surfaces of the respective barrier sheets 93. Sections of the proximal zones 97 of the respective barrier sheets 93 extending transversely outward beyond the respective side edges 92 of the panel 79 are folded back transversely inward along the respective side edges 92, interposed between the first backsheet 78 and the second backsheet 88 and bonded to the inner and outer surfaces of these sheets 78, 88, respectively.

With the article 70 put on the wearer's body, the distal edges 102 of the distal zones 98 of the respective barrier sheets 93, in the crotch region 22, come close to or in contact with the wearer's inguinal region and the segments of the distal edges 102 extending from the crotch region 72 into the rear waist region 73 further go into the wearer's buttock cleavage so as to come close to or in contact with both sides of the anus in the same manner as illustrated by FIGS. 8 and 9. With the article 70 put on the wearer's body, feces discharged therein are received in the feces receiving space 105 and the pocket 112 through a clearance defined between the distal edges 102 of the respective distal zones 98. Feces received in this manner are coved from above with the distal zones 98. Urine discharged between the distal edges 102 of the distal zones 98 is absorbed and retained by the core 89 after permeation through the topsheet 87.

In the article 70, the dimension by which the distal edges 102 of the distal zones 98 are spaced from each other is gradually reduced from the crotch region 72 toward the rear waist region 73, the feces receiving space 105 is formed between the topsheet 87 and the distal zones 98 of the respective barrier sheets 93, and the pocket 112 is formed between the topsheet 87 and the end sheet 104. Such an arrangement ensures that feces discharged in the article 70 is received in the space 104 and the pocket 112 and covered from above with the distal zones 98 of the respective barrier sheets 93 extending over the crotch region 72 and the rear waist region 73 and the end sheet 104. In other words, it is unlikely that feces discharged in the article 70 might be exposed between the distal zones 98 and come in contact with the wearer's crotch region and/or buttock. Consequentially, the wearer's crotch region and buttock are protected against any amount of feces possibly clinging thereto and thus the wearer's skin is protected against contamination with feces. The article 70 allows the distal zones 98 of the respective barrier sheets 93 to prevent urine as well as feces from moving sideways and thereby to prevent urine as well as feces from leaking beyond the transversely opposite side edges 92. At the same time, movement of feces in the longitudinal direction is intercepted by the end sheet 104 and there is no anxiety that any amount of feces discharged in the article 70 might leak from the rear waist region 73.

In the article 70, the end sheet 104 including the portion 111 which is stretchable and contractible in the transverse direction is attached to the distal zones 98 of the respective barrier sheets 93 in stretchable and contractible manner. Such an arrangement ensures that, even if movement of the article wearer biases the distal zones 98 extending aside toward the rear ends 100 to move in the transverse direction, contractile force of the end sheet 104 functions to hold the distal edges 102 of the distal zones 98 around the transverse middle of the crotch region 72 and thereby to restrain movement of the distal zones 98. With the article 70 put on the wearer's body, it is thus ensured that the distal zones 98 extending aside toward the rear ends 100 do not significantly shift away from the predetermined positions. In other words, the distal edges 102 of the distal zones 98 are maintained close to or in contact with the inguinal region as well as both sides of the anus of the wearer. In this way, it is ensured that feces discharged in the article 70 are reliably received in the feces receiving space 105 and the pocket 112 through the clearance defined between the distal edges 102.

With the article 70 put on the wearer's body, even if the first backsheet 78 is distorted due to movement of the wearer transmitted to this first backsheet 78, it is unlikely that the core 89 having a rigidity higher than that of the sheet 78 might be distorted to move the distal zones 98 of the respective barrier sheets 93 having the base points for rising up defined inside the transversely opposite side edges 116 of the core 89. With the article 70 put on the wearer's body, there is no anxiety that the distal zones 98 of the respective barrier sheets 93 might significantly move and the dimension by which the distal edges 102 of the distal zones 98 are spaced from each other might significantly change. Therefore it is ensured that feces discharged in the article 70 pass through the clearance defined between the distal edges 102 of the respective distal zones 98 and is received by the feces receiving space 105 and the pocket 112.

In the article 70, the minimum dimension L1 by which the distal edges 102 (See FIG. 15) of the respective distal zones 98 extending aside toward the rear ends 100 are spaced from each other is in a range of 0 to 25%, preferably 0 to 10%, more preferably 0 to 5% of the minimum transverse dimension L3 (See FIG. 17) of the core 89 extending in the crotch region 72. If the minimum dimension L1 by which the distal edges 102 are spaced from each other exceeds 25% of the minimum transverse dimension L3 of the core 89, it will be difficult for the distal zones 98 to cover feces sufficiently from above. As a result, feces will be exposed between the distal zones 98 and feces may cling to the wearer's inguinal region and buttock to contaminate the wearer's skin over a wide extent. In the article 70, the maximum dimension L2 (See FIG. 15) by which the distal edges 102 of the distal zones 98 extending aside toward the side of the front ends 99 is in a range of 26 to 120%, preferably 30 to 80% of the minimum transverse dimension L3 (See FIG. 17) of the core 89 extending in the crotch region 22. If the maximum dimension L2 by which the distal edges 102 are spaced from each other is less than 26% of the minimum transverse dimension L3, the dimension by which the distal edges 102 are spaced from each other will be insufficient to prevent discharge of urine from occurring outside the distal zones 98. So far as the article 70 for baby is concerned, specific values of the minimum dimension L1, maximum dimension L2 by which the distal edges 102 are spaced from each other are the same as those having been described with reference to the article 20A of FIG. 1. Specific values of the minimum dimension L1, maximum dimension L2 by which the distal edges 102 are spaced from each other in the article 70 for adult are also the same as those having been described with reference to the article 20A of FIG. 1.

As a stock material for the topsheet 29, 87, not only the hydrophilic fibrous nonwoven fabric 35, 94 but also a hydrophobic fibrous nonwoven fabric having a plurality of apertures may be used. As a stock material for the backsheet 30, 78, 88 and the barrier sheets 34, 93 and the end sheet 45, 104, a breathable liquid-impervious plastic film or a composite sheet consisting of a breathable liquid-impervious plastic film and a hydrophobic fibrous nonwoven fabric laminated together also may be used. In addition, a composite nonwoven fabric (e.g., SM nonwoven fabric, SMS nonwoven fabric) consisting of a spun bond fibrous nonwoven fabric having high strength as well as good flexibility laminated on at least one surface of a melt blown fibrous nonwoven fabric having high water-resistance may be also used as a stock material for the end sheet 45, 104. It is also possible to use, as a stock material for the end sheet 45, 104, an elastic fibrous nonwoven fabric made of elastic fibers obtained by a melt spinning thermoplastic elastomer resin may be used. It is also possible to use a composite nonwoven fabric consisting of a hydrophilic fibrous nonwoven fabric made of crimped fibers laminated on at least one surface of an elastic fibrous nonwoven fabric.

The fibrous nonwoven fabric may be selected from the group consisting of a spun lace nonwoven fabric, a needle punch nonwoven fabric, a melt blown nonwoven fabric, a thermal bond nonwoven fabric, a spun bond nonwoven fabric and a chemical bond nonwoven fabric. The hydrophilic fibrous nonwoven fabric may be made of any one of synthetic fibers modified to become hydrophilic, semi-synthetic fibers and regenerated fibers, or composite fibers consisting of a mixture thereof. The hydrophobic fibrous nonwoven fabric may be made of synthetic fibers. The hydrophobic fibrous nonwoven fabric may contain therein water repellent treated semi-synthetic fibers or regenerated fibers. While not specified, the synthetic fibers may be selected from the group consisting of polyester-, polyacrylonitrile-, polyvinylchloride-, polyethylene-, polypropylene- and polystyrene-based synthetic fibers. It is also possible to use, as synthetic fibers, core-sheath-type composite fibers, parallel-type composite fibers, modified macaroni fibers, micro-porous fibers or conjugative type composite fibers.

Bonding of the sheets 29, 87, 30, 78, 88, 34, 93, 45, 104 one to another, bonding of the core 31, 89 to the sheets 29, 30, 87, 88, bonding of the elastic members 32, 33, 44, 48, 85, 86, 103, 107 to the sheets 34, 45, 93, 104 and/or the nonwoven fabric layers 36, 37, 47, 83, 84, 106 may be carried out using adhesive. The sheets 29, 87, 30, 78, 88, 34, 93, 45, 104 and the nonwoven fabric layers 36, 37, 47, 83, 84, 106 are coated with adhesive preferably in the pattern such as spiral, wavy, zig-zag, dotted or striped pattern. By coating the sheets 29, 87, 30, 78, 88, 34, 93, 45, 104 and the nonwoven fabric layers 36, 37, 47, 83, 84, 106 with adhesive in such pattern, these sheets 29, 87, 30, 78, 88, 34, 93, 45, 104 are intermittently bonded one to another, the cores 31, 89 are intermittently bonded to the sheets 29, 30, 87, 88, and the elastic members 32, 33, 44, 48, 85, 86, 103, 107 are intermittently bonded to the sheets 34, 45, 93, 104 and the nonwoven fabric layers 36, 37, 47, 83, 84, 106. Adhesive may be selected from the group consisting of hot melt adhesive, acrylic adhesive and rubber-based adhesive.

What is claimed is:

1. A disposable wearing article, comprising:
a front waist region;
a rear waist region;
a crotch region extending between said waist regions;
a pair of longitudinally opposite ends extending in a transverse direction of said article;
a pair of transversely opposite lateral margins extending in a longitudinal direction of said article;
opposite body-side and garment-side surfaces;
a liquid-absorbent core at least in said crotch region for absorption and containment of bodily fluids, said core being sandwiched between the body-side surface and the garment-side surface:
a pair of liquid-impervious barrier sheets laid on the body-side surface in at least said crotch region among said front and rear waist regions and said crotch region, said barrier sheets comprising (a) proximal zones lying along said lateral margins of said article so as to extend in the longitudinal direction, (b) elasticized distal zones extending in the longitudinal direction and normally biased to rise up above said body-side surface, and (c) longitudinally opposite front and rear ends bonded to said body-side surface; and an elasticized end sheet positioned toward said rear ends and between said distal zones, and adapted to pull said distal zones closer to each other, wherein said end sheet comprises (1) opposite lateral segments that are directly bonded to said distal zones when said elasticized end sheet is being stretched in the transverse direction so that said distal zones are pulled towards each other in the transverse direction by the so bonded elasticized end sheet and (2) an intermediate segment extending in the transverse direction between said opposite lateral segments and being free of direct attachment to said barrier sheets;

wherein a dimension, by which distal edges of said distal zones are spaced from each other in the transverse direction, increases gradually in a direction from said rear ends toward said front ends of said liquid-barrier sheets; and wherein said end sheet extends in the transverse direction without obstructing, in use, movement of body discharges on the body-side surface in the longitudinal direction from said crotch region to the front waist region, and further comprises:

a rear portion which, in a region rearward of said core and along a rear end of said rear waist region, is sandwiched between and bonded directly to (i) the rear ends of the barrier sheets and (ii) a topsheet defining said body-side surface; and a front portion which spans a gap between the distal edges of said distal zones and defines, together with the distal zones of the barrier sheets, a top wall of a pocket that opens forwardly for receiving fecal material in use.

2. The wearing article as defined by claim 1, wherein a minimum dimension by which the distal edges of said distal zones are spaced from each other in the transverse direction being in a range of 0 to 25% of a minimum transverse dimension of said core extending in said crotch region, and a maximum dimension by which the distal edges of said distal zones are spaced from each other in the transverse direction being in a range of 26 to 120% of the minimum transverse dimension of said core extending in said crotch region.

3. The wearing article as defined by claim 1, wherein said barrier sheets have said front and rear ends bonded to said body-side surface with said front ends folded outward in the transverse direction and with said rear ends directed inward in the transverse direction.

4. The wearing article as defined by claim 1, wherein the intermediate segment of said end sheet in the front portion of said end sheet is entirely spaced upward from the body-side surface as said distal zones rise up above said body-side surface.

5. The wearing article as defined by claim 1, wherein the intermediate segment of said end sheet in the front portion of said end sheet is entirely free of direct attachment to said body-side surface.

6. The wearing article as defined by claim 1, wherein the front portion of the end sheet further defines a rear wall of the pocket, the distal zones of the barrier sheets define side walls of the pocket, and the body-side surface defines a bottom of the pocket; and the front portion of the end sheet is adapted to cover, from above, fecal material received in the pocket.

7. The wearing article as defined by claim 1, wherein each of the lateral segments of the end sheet at the front portion of said end sheet is bonded to inner surfaces of the distal zone and the proximal zone of the respective barrier sheet, as well as the body-side surface defined by said topsheet; and said inner surfaces of the distal zone and the proximal zone face the absorbent core.

8. The wearing article as defined by claim 1, further comprising elastic members contractible in the transverse direction and directly attached to the end sheet along a front end of the front portion thereof so as to render said end sheet elasticized.

9. The wearing article as defined by claim 8, wherein said end sheet extends forwardly in the longitudinal direction from the rear portion located in the rear waist region into the crotch region and terminates at the front end of the front portion, without extending beyond a longitudinal middle of said crotch region.

10. The wearing article as defined by claim 8, wherein along one of said elastic members, each of the lateral segments of the end sheet at the front portion of said end sheet is bonded to an inner surface of the respective distal zone over substantially an entire width of said respective distal zone in the transverse direction;

said inner surface of the distal zone faces the absorbent core.

11. A disposable wearing article, comprising:

a front waist region;

a rear waist region;

a crotch region extending between said waist regions;

a pair of longitudinally opposite ends extending in a transverse direction of said article;

a pair of transversely opposite lateral margins extending in a longitudinal direction of said article;

opposite body-side and garment-side surfaces;

a pair of liquid-impervious barrier sheets laid on the body-side surface in at least said crotch region among said front and rear waist regions and said crotch region, said barrier sheets comprising (a) proximal zones lying along said lateral margins of said article so as to extend in the longitudinal direction, (b) elasticized distal zones extending in the longitudinal direction and normally biased to rise up above said body-side surface, and (c) longitudinally opposite front and rear ends bonded to said body-side surface; and an elasticized end sheet positioned toward said rear ends and between said distal zones, and adapted to pull said distal zones towards each other by being bonded to said distal zones when said elasticized end sheet is being stretched in the transverse direction, wherein said end sheet comprises (1) opposite lateral segments directly bonded to said distal zones and (2) an intermediate segment extending in the transverse direction between said opposite lateral segments and being free of direct attachment to said barrier sheets;

wherein a dimension, by which distal edges of said distal zones are spaced from each other in the transverse direction, increases gradually in a direction from said rear ends toward said front ends of said liquid-barrier sheets; and wherein said end sheet further comprises:
a rear portion which is sandwiched between (i) the rear ends of the barrier sheets and (ii) a topsheet defining said body-side surface of the article; and
a front portion which spans a gap between the distal edges of said distal zones and defines, together with the distal zones of the barrier sheets, a top wall of a pocket that opens forwardly for receiving fecal material in use.

* * * * *